(12) United States Patent
Reaney et al.

(10) Patent No.: US 8,383,172 B2
(45) Date of Patent: Feb. 26, 2013

(54) RECOVERY OF HYDROPHOBIC PEPTIDES FROM OILS

(75) Inventors: Martin J. Reaney, Saskatoon (CA); Yunhua Jia, Saskatoon (CA); Jianheng Shen, Saskatoon (CA); Cynthia Schock, Saskatoon (CA); Nancy Tyler, Saskatoon (CA); Jim Elder, Saskatoon (CA); Sarabjeet Singh, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 12/747,160

(22) PCT Filed: Dec. 22, 2008

(86) PCT No.: PCT/CA2008/002272
§ 371 (c)(1),
(2), (4) Date: Jan. 6, 2011

(87) PCT Pub. No.: WO2009/079792
PCT Pub. Date: Jul. 2, 2009

(65) Prior Publication Data
US 2011/0111073 A1  May 12, 2011

Related U.S. Application Data

(60) Provisional application No. 61/008,604, filed on Dec. 21, 2007.

(51) Int. Cl.
*A61K 36/00* (2006.01)
*A61K 36/55* (2006.01)
(52) U.S. Cl. .......................... 424/768; 424/724
(58) Field of Classification Search .................. None
See application file for complete search history.

(56) References Cited

U.S. PATENT DOCUMENTS
2007/0098854 A1* 5/2007 Van Lengerich et al. ....... 426/99

FOREIGN PATENT DOCUMENTS
JP    09165399 A  *  6/1997
WO    9007523 A1     7/1990

OTHER PUBLICATIONS

Bruhl et al, Identification of bitter off-taste compounds in the stored cold pressed linseed oil, Journal of agricultural and food chemistry, (Sep. 19, 2007) vol. 55, No. 19, pp. 7864-7868.*

Stefanowicz, Electrospray mass spectrometry and tandem mass spectrometry of the natural mixture of cyclic peptides from linseed, European journal of mass spectrometry (Chichester, England), (2004) vol. 10, No. 5, pp. 665-671.*
Bruhl, Ludger; Matthaus, Bertrand; Fehling, Eberhard; Wiege, Berthold; Lehmann, Britta; Luftmann, Heinrich; Bergander, Klaus; Quiroga, Kathrin; Scheipers, Anne; Frank, Oliver; Hofmann Thomas,; "Identification of Bitter Off-Taste Compounds in the Stored Cold Pressed Linseed Oil", Journal of Agricultural and Food Chemistry, 2007, 7864-7868, 55.
Tan, Ning-Hua; Zhou, Jun, "Plant Cyclopeptides", Chemical Reviews, 2006, 840-895, vol. 106, No. 3.
McCluskey, Adam; Sim, Alistair T.R.; Sakoff, Jennette A., "Serine-Threonine Protein Phosphatase Inhibitors: Development of Potential Therapeutic Strategies", Journal of Medicinal Chemistry, Mar. 14, 2002, 1151-1175, vol. 45, No. 6.
Matsumoto, Teruki; Shishido, Akira; Morita, Hiroshi; Itokawa, Hideji; Takeya, Koichi, "Conformational analysis of cyclolinopeptides A and B", Tetrahedron, 2002, 5135-5140, 58, Elsevier Science Ltd., Pergamon.
Matsumoto, Teruki; Shishido, Akira; Morita, Hiroshi; Itokawa, Hideji; Takeya, Koichi, "Cyclolinopeptides F-I, cyclic peptides from linseed", Phytochemistry, 2001, 251-260, 57, Elsevier Science Ltd., Pergamon.
Stefanowicz, Piotr, "Detection and sequencing of new cyclic peptides from linseed by electrospray ionization mass spectrometry", Acta Biochimica Polonica, 2001, 1125-1129, vol. 48, No. 4.
Morita, Hiroshi; Shishido, Akira; Matsumoto, Teruki; Itokawa, Hideji; Takeya, Koichi, "Cyclolinopeptides B—E, New Cyclic Peptides from *Linum usitatissimum*", Tetrahedron, 1999, 967-976, 55, Elsevier Science Ltd., Pergamon.
Wieczorek, Z. et al., "Immunosuppressive activity of Cyclolinopeptide A", Peptide Research, 1991, 275-283, vol. 4, No. 5.
Morita et al., Bioorganic & Medicinal Chemistry Letters, 1997, 1269-1272, vol. 7, No. 10.

* cited by examiner

*Primary Examiner* — Qiuwen Mi
(74) *Attorney, Agent, or Firm* — Bereskin & Parr LLP/S.E.N.C.R.L., s.r.l.; Patricia Folkins

(57) ABSTRACT

Methods for separation and recovery of individual cyclic peptides from plant materials, said method comprising the steps of: (a) extracting an oil from a plant material; (b) separating the extracted oil into a non-polar fraction and a polar fraction; (c) separation and recovery of cyclic peptides from the non-polar fraction, and (d) separation and recovery of cyclic peptides from the polar fraction. The methods are suitable for separation and recovery of individual cyclolinopeptides from flax seed oil. Individual cyclolinopeptides are useful for modulation physiological disorders associated with apoptosis. Modified flaxseed oils may be produced by commingling flaxseed oils absent cyclolinopeptides, with at least one cyclolinopeptide separated and recovered with the methods disclosed herein.

20 Claims, 28 Drawing Sheets

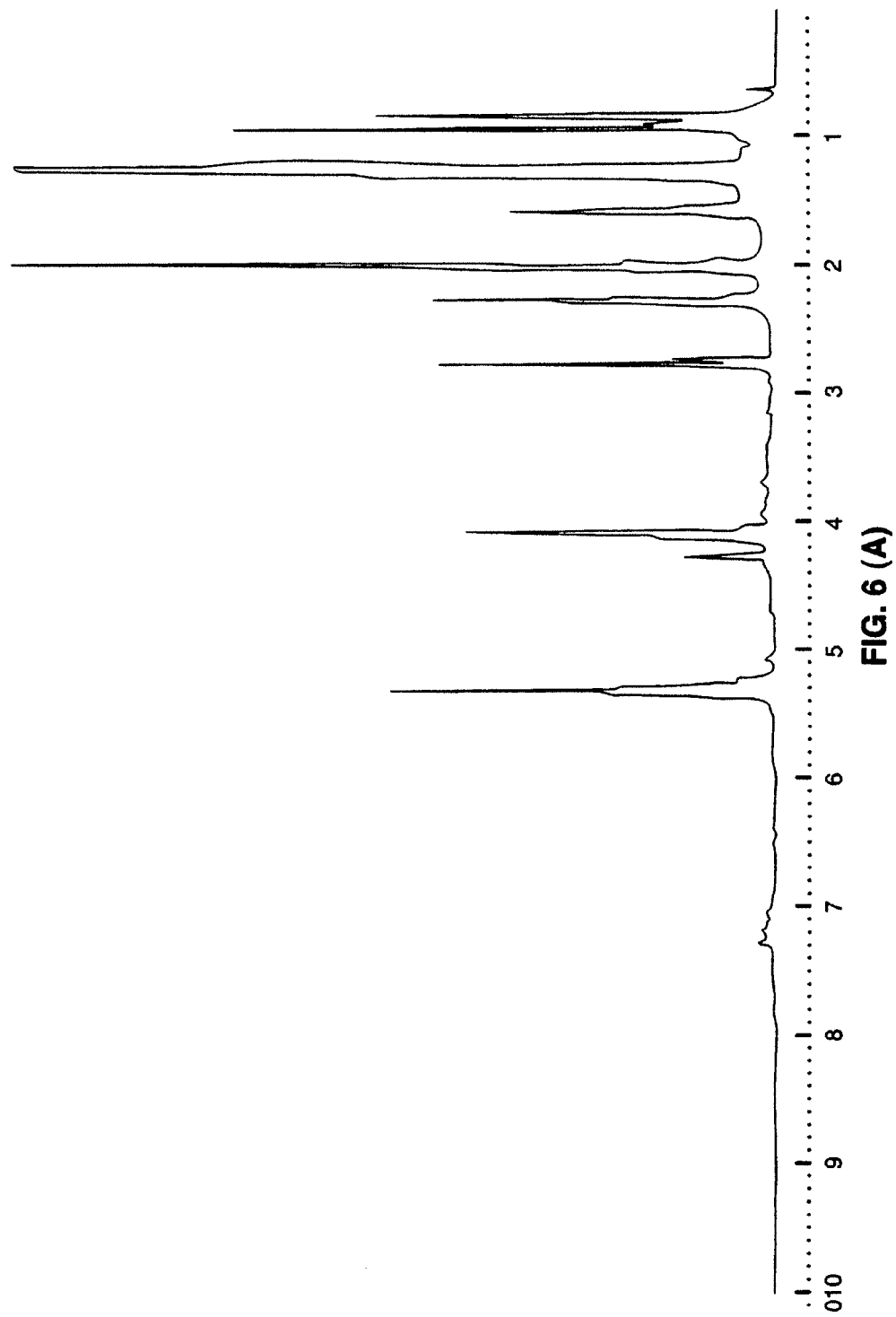

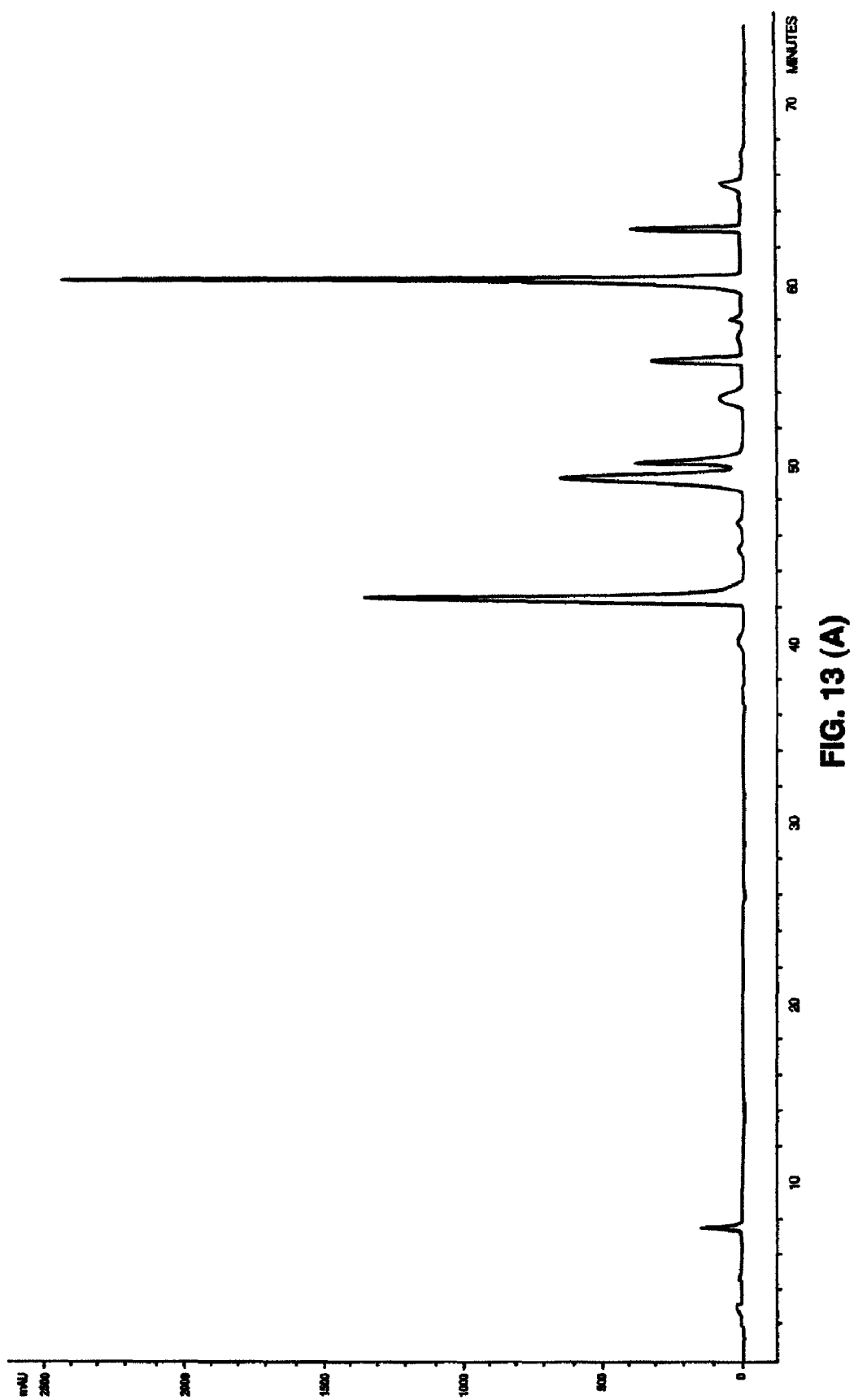

```
                     SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: Synthetic construct - P21 primer

<400> SEQUENCE: 1
atgtcagaac cggctggg                                                      18

<210> SEQ ID NO 2
<211> LENGTH: 18
<212> TYPE: DNA
<213> ORGANISM: Artificial Sequence
<220> FEATURE:
<223> OTHER INFORMATION: Synthetic construct - P21 primer

<400> SEQUENCE: 2
tcccaggcga agtcaccc                                                      18

<210> SEQ ID NO 3
<211> LENGTH: 21
<212> TYPE: DNA
<213> ORGANISM: Artificial Sequence
<220> FEATURE:
<223> OTHER INFORMATION: Synthetic construct - PUMA primer

<400> SEQUENCE: 3
atgaaatttg gcatggggtc t                                                  21

<210> SEQ ID NO 4
<211> LENGTH: 16
<212> TYPE: DNA
<213> ORGANISM: Artificial Sequence
<220> FEATURE:
<223> OTHER INFORMATION: Synthetic construct - PUMA primer

<400> SEQUENCE: 4
gcctggtgga ccgccc                                                        16

<210> SEQ ID NO 5
<211> LENGTH: 15
<212> TYPE: DNA
<213> ORGANISM: Artificial Sequence
<220> FEATURE:
<223> OTHER INFORMATION: Synthetic construct - GAPDH primer

<400> SEQUENCE: 5
atggggaagg tgaag                                                         15
```

```
<210> SEQ ID NO 6
<211> LENGTH: 18
<212> TYPE: DNA
<213> ORGANISM: Artificial Sequence
<220> FEATURE:
<223> OTHER INFORMATION: Synthetic construct - GAPDH primer

<400> SEQUENCE: 6
gacaagcttc ccgttctc                                                 18

<210> SEQ ID NO 7
<211> LENGTH: 20
<212> TYPE: DNA
<213> ORGANISM: Artificial Sequence
<220> FEATURE:
<223> OTHER INFORMATION: Synthetic construct - BCL-2 primer

<400> SEQUENCE: 7
atggcgcacg ctgggagaac                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct - BCL-2 primer

<400> SEQUENCE: 8
gcgaccgggt cccgggatgc                                               20
```

RECOVERY OF HYDROPHOBIC PEPTIDES FROM OILS

INCORPORATION OF SEQUENCE LISTING

A computer readable form of the Sequence Listing "13764-129_SequenceListing.txt" (8,192 bytes), submitted via EFS-WEB and created on Apr. 30, 2012, is herein incorporated by reference.

FIELD OF THE INVENTION

The present invention relates to methods for recovery of hydrophobic peptides from plant oils. More specifically, the invention relates to methods for separating and isolating individual hydrophobic peptides from oils extracted from plant materials.

BACKGROUND OF THE INVENTION

Many hydrophobic peptides from plants are known to be highly biologically active materials with wide ranges of therapeutic applications. For example, asterins are cyclopentapeptides isolated from *Aster tartaricus* (also known as tartarian aster), known to be potent anti-tumour compounds. Cyclic heptapeptides extracted from *Stellaria yunnanensis* (also known as chickweed), commonly referred to as yunnanins, have cytotoxic effects on P388 leukemia cells. Likewise, *Rubia akane* (also known as asian madder) and *Rubia cordifolia* (also known as indian madder) produce bicyclic hexapeptides with similar cytotoxic activities. Segetalin A is a cyclic hexapeptide from *Vaccaria segitalis* (also known as Wang Bu Liu Xing or cow cockle) known to have estrogen-like activity. *Pseudostellaria heterophylla* (also known as Tai Zi Shen, false starwort or Prince Seng) is used as the "ginseng of the lungs." *P. heterophylla* is known to contain the cyclic heptapeptide Pseudostellarin D, a well-known Chinese traditional medicine that is used to tonify the "qi" and generate "yin" fluids. The use of Pseudostellarin D as a lung and spleen tonic stems from its inhibition of tyrosinase. In addition, cyclolinopeptides from flax seed are active in suppressing a wide range of immunological responses, including: (i) delayed-type hypersensitivity response; (ii) skin allograph rejection; (iii) graft versus host reaction; (iv) post-adjuvant arthritis; and (v) haemolytic anemia of New Zealand black (NZB) mice.

Potential applications of hydrophobic peptides include, but are not limited to, their use in drug forms and in vaccine formulations. Expression of the genes encoding the cyclolinopeptides is associated with programmed cell death in times of injury to a cell. Accordingly, the recovery and purification of such hydrophobic peptides is important. To date, reported methods and processes for recovery of hydrophobic peptides are cumbersome and do not result in a significant yield of hydrophobic peptides. Moreover, prior inventions involve the extraction of all hydrophobic peptides as a group using silica gel, followed by chromatographic separation in order to isolate individual hydrophobic peptides, which can be problematic and expensive.

Kaufman et al. (Uber ein Oligopeptid aus Leinsamen Chem Ber, 1959, 92: 2805-9) describe a method of recovery of hydrophobic peptides from a precipitated "slime" obtained in the processing of flax seed. Morita et al. (Bioorganic & Medicinal Chemistry Letters, 1997, 7(10): 1269-1272; Tetrahedron, 2002, 58: 5135-5140; Phytochemistry, 2001, 57: 251-260; Tetrahedron, 1999, 55: 967-976) describe the preparation of small amounts of hydrophobic peptides from flax seed, press cake and roots. Their extraction process requires significant quantities of flax material (30 kilograms) extracted with four volumes of hot methanol. The solvent is subsequently removed and the entire mixture subjected to chromatography on a polystyrene column (Diaion™ HP-20) and washed with increasing concentrations of methanol. The hydrophobic peptides remain bound to the column until washed with pure methanol. Polar solutes can be removed from the column in the presence of water. The methanol fraction containing the hydrophobic peptides is then subjected to normal phase silica gel chromatography using a gradient of chloroform and methanol (100:0 to 0:100), wherein the peptides are eluted with relatively low concentrations of methanol. A fraction of the methanol:chloroform gradient is recovered and subjected to reverse-phase chromatography using a methanol and acetonitrile gradient to isolate individual fractions containing individual hydrophobic peptides.

Stefanowicz (Acta Biochimica Polonica, 2001, 48: 1125-1129) disclose recovery of hydrophobic peptides from flax seed. The extraction of cyclolinopeptides is done using 5 grams of ground flax seed, extracted overnight in 100 milliliters of acetone. The acetone fraction is concentrated in vacuo and the resulting mixture dissolved in methanol and hydrolyzed using 10% sodium hydroxide. After drying, the fraction containing the cyclolinopeptides is isolated by ethyl acetate extraction. Such a process does not allow the separation and isolation of each hydrophobic peptide.

A recent publication by Brühl et al. (J. Agric. Food Chem., 2007, 55: 7864-7868) disclose a method for isolating hydrophobic cyclopeptides which provides low yields of product. Bitter linseed oil is prepared from seeds with a laboratory screw press with an 8-mm nozzle at temperatures not exceeding 60° C. and a speed of screw rotation of 35 rpm. The temperature of the freshly obtained oil (30% yield) does not exceed 40° C. No additional steps are taken to maximize oil recovery and peptide extraction from the seeds. An aliquot of the bitter linseed oil is subsequently dissolved in heptane, a solvent not approved for food extraction, and then extracted 3 times with methanol/water solvent (6:4; v/v; 200 mL each). The aqueous layers are filtered through a wet filter paper to separate traces of oil from the layer, and the solvent is then removed in vacuum. A bitter-tasting fraction is obtained from the oil, which is then dissolved in methanol/diethyl ether (1:1; v/v; 1 mL) and placed onto the top of a glass column filled with a slurry of silica gel. Chromatography is performed with solvent mixtures using ratios of diethyl ether and ethanol. The individual fractions are freed from the solvent under vacuum and then taken up in water. Purification of cyclolinopeptide E is accomplished by reverse-phase high-performance liquid chromatography (HPLC). Aliquots of certain fractions thought to contain the bitter-taste compound are dissolved in water/ethanol and separated by HPLC on a column connected to a UVD 340-type US/vis detector operating at a wavelength of 210 nm. Chromatography is performed starting with a mixture of methanol/water (75:25; v/v) and ending with 100% methanol within 25 minutes. The effluent is collected in 1-min fractions using a fraction collector, with each fraction freed from solvent and residues taken up in water upon ultrasonication.

The recovery of hydrophobic peptides from plants is difficult, laborious, and expensive. Chemical synthesis of the peptides has been considered as an alternative source for candidate therapeutic hydrophobic peptides. For example, Wiezorek et al. (Peptide Res, 1991, 4: 275-283) disclose synthetic preparation of cyclolinopeptide A on Merrifield resin using tert-butyloxycarbonyl protected amino acids. The product is split from the resin by a mixture of trifluoro acetic acid and sulphuric acid and then cyclized by Castro's reagent, dissolved in ethyl acetate and subsequently washed with 1N NaOH, 1N HCl and water. The final product is purified by HPLC. However, the product yields of such synthetic methods are also very low, and are not adequate solutions to the difficulties encountered with recovering endogenous peptides.

SUMMARY OF THE INVENTION

The exemplary embodiments of the present invention related to methods for recovering hydrophobic peptides from plant oils. Suitable oils are exemplified by flaxseed oil An exemplary embodiment of the present invention relates to methods for separation and recovery of individual cyclic peptides from plant materials. Suitable plant materials are oils extracted therefrom. The methods generally comprise the steps of: (a) extracting an oil from a plant material; (b) separating the extracted oil into a non-polar fraction and a polar fraction; (c) separation and recovery of cyclic peptides from the non-polar fraction, and (d) separation and recovery of cyclic peptides from the polar fraction.

According to one aspect, the hydrophobic peptides are recovered from a selected plant oil by commingling the oil with a suitable adsorbent whereby the hydrophobic peptides are attached to the adsorbent. A suitable adsorbent is exemplified by silica. After the oil is separated from the adsorbent, the adsorbent is washed at least once with a suitable solvent selected for solubilising at least one plurality of hydrophobic peptides attached to the adsorbent. The one plurality of hydrophobic peptides is recovered from the solvent. It is optional to sequentially flow a series of solvents through the adsorbent whereby each solvent is selected for solubilising at least one plurality of hydrophobic peptides attached to the adsorbent.

According to another aspect, suitable solvents are exemplified by hydrocarbons, ketones, lower aliphatic alcohols, esters, halogenated solvents, ethers, aromatics, and combinations thereof. It is suitable for a series of solvents to comprise increasing polarity.

Another exemplary embodiment of the present method relates to modified oils comprising tailored compositions of one or more selected hydrophobic peptides, and to methods for producing such modified oils. One or more selected hydrophobic peptides separated, purified and quantified as disclosed herein, is/are commingled with a plant oil absent hydrophobic peptides.

Another embodiment of the present invention relates to methods for modulation of physiological disorders associated with apoptosis, with compositions comprising one or more of the purified hydrophobic peptides produced as disclosed herein.

BRIEF DESCRIPTION OF THE DRAWINGS

The present invention will be described in conjunction with reference to the following drawings, in which.

DETAILED DESCRIPTION OF THE INVENTION

Figure 1:
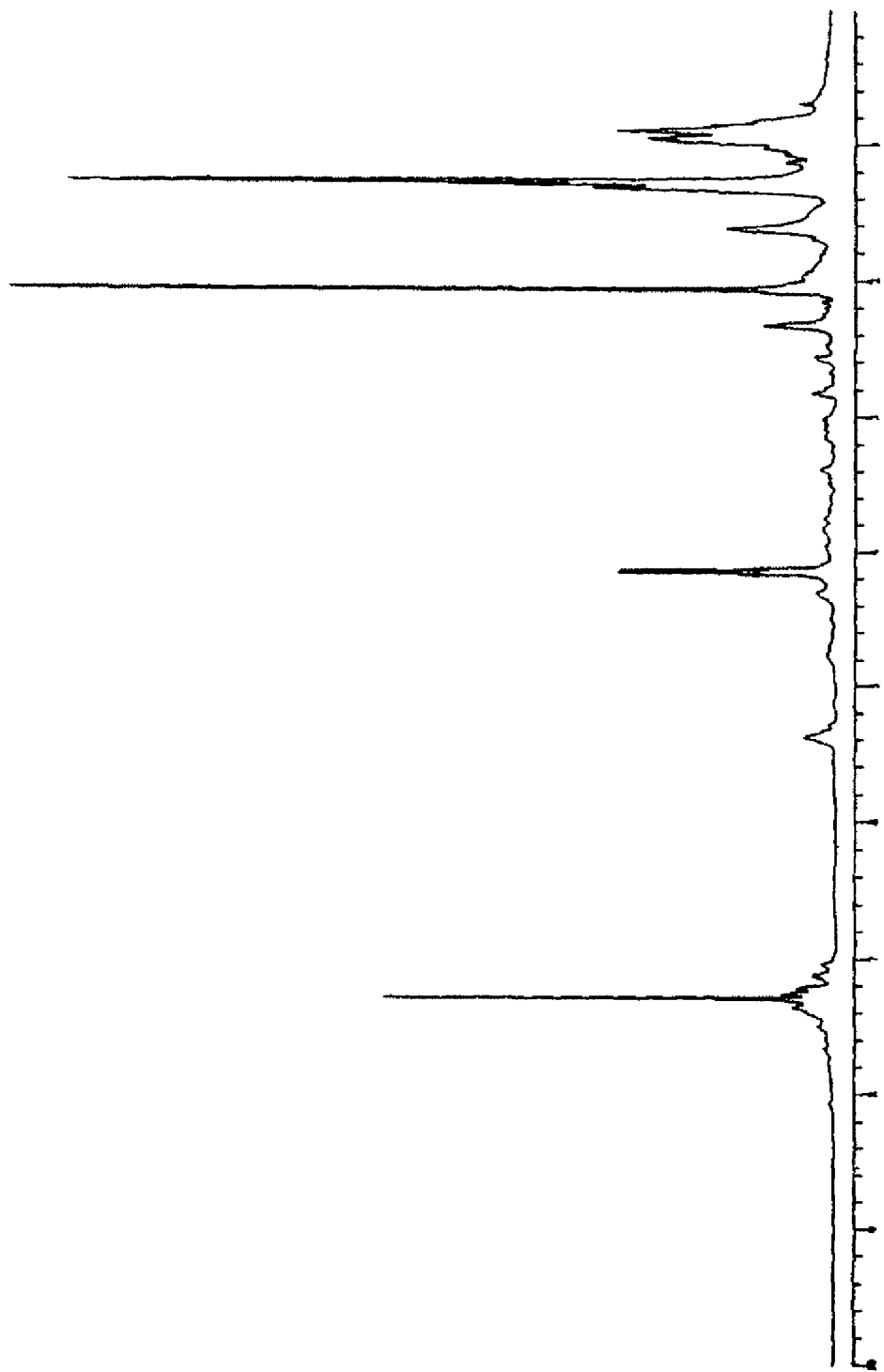
FIG. 1 is a NMR spectroscopy chart of cyclolinopeptides extracted from flaxseed oil and separated by elution from a silica chromatography column according to an embodiment of the present invention.

The present invention relates to methods for recovering and concentrating significant yields of individual hydrophobic peptides from biological solvents such as oil, fat, wax and grease. The peptides may be extracted from plant materials exemplified by flaxseed that contain high endogenous levels of biological solvents, or from materials that contain small amounts of endogenous biological solvents.

Certain hydrophobic peptides isolated from plants are known to possess biological activity with potential therapeutic applications for various mammalian physiological conditions. Cyclolinopeptides from flaxseed oils, in particular, may affect programmed cell death or apoptosis, to protect multicellular organisms in response to stress signals as may be produced by injury or shock. Apoptosis, that is, a control mechanism for cell death is required throughout all stages of the life cycle. Excessive apoptosis may lead to hypotrophy, while insufficient apoptosis may allow excessive cell division, as observed in cancer. Apoptosis regulating plant compounds exemplified by cyclolinopeptides are sought-after as potential chemotherapy agents. Accordingly, methods for the recovery and purification of such hydrophobic peptides that have potential for regulating apoptosis in cells, particularly for inducing apoptosis in cells, are useful and desirable. Furthermore, the isolation of individual hydrophobic peptides from a pool of hydrophobic peptides extracted from a plant is preferable since each individual peptide may have a different biological activity and effect on gene expression in cells.

Accordingly, the present invention relates to methods for recovery of individual hydrophobic peptides from oils extracted from plant material, wherein hydrophobic peptides are readily enriched or recovered from biological material. The present invention relates to methods that are less laborious and produce greater yields of product than methods currently available to those skilled in these arts.

An exemplary embodiment of the present invention relates to a simplified method for the recovery of individual hydrophobic peptides. Methods commonly used for the recovery of hydrophobic peptides involve the extraction of oil from significant quantities of plant material, which do not result in large yields of peptides. The methods of the present invention disclosed herein employ strategies for extraction of substantial amounts of oils from plant materials wherefrom substantial amounts of individual hydrophobic peptides are extractable. Physical methods are used to increase the solubility of the hydrophobic peptides in the oils. Such methods include, but are not limited to, pressing, grinding, emulsifying, extruding, blending, and exposure to ultra-sound waves, microwaves, and infrared radiation. It is within the scope of the invention to include other physical treatments exemplified by tempering, and exposure to microwave or infrared radiation. Hydrophobic peptides are known to be sensitive to oxidation. The methods according to the present invention limit the exposure of the peptides and the source plant materials to oxygen during extraction and separation, such methods including blanketing the peptide source material in oxygen-depleted atmospheres prior to and during extraction of the oils. As an example, removal of air by vacuum or replacement of the atmosphere above the solutions comprising hydrophobic peptides, significantly improves the stability of the separated hydrophobic peptides.

An exemplary embodiment of the present invention relates to the separation of extracted oil into more polar fractions and less polar fractions. We have determined that this is advantageous since spectroscopic analyses of the polar fractions and the non-polar fractions indicate that cyclic peptides vary considerably in polarity, and that very low polarity peptides remain with the non-polar fraction while higher-polarity peptides are concentrated into polar fractions. Consequently, separation of oils into polar and non-polar fractions will concentrate the lower polarity hydrophobic peptides into the non-polar fractions wherefrom they may be controllably and selectively separated by flowing the non-polar fractions through chromatography equipment.

It is within the scope of the present invention to configure and modify the methods to enable, if so desired, a single-step separation of the peptides from oils. A suitable modification is exemplified by the addition and intermixing of silica directly with the extracted oil wherein the hydrophobic peptides will attach to the silica. The oil is then separated from the peptide-laden silica. The peptide-laden silica may be washed sequentially with a series of increasing polarity solvents, wherein each solvent is selected for solubilisation and elution of certain specific peptides. Alternatively, silica may be added into and intermixed with the non-polar fractions separated from the extracted oils after which, the peptide-laden silica is separated from the non-polar fraction. The peptide-laden silica may be washed sequentially with a series of increasing polarity solvents, wherein each solvent is selected for solubilisation and elution of certain specific peptides. Another suitable option is to flow each eluted fraction solubilized from the peptide-laden silica, through chromatography equipment to further separate and purify individual hydrophobic peptides. Those skilled in these arts will recognize the potential of utilizing large-scale preparative chromatography separation methods such as simulated moving bed chromatography of centrifugal partition chromatography. The scope of the present invention encompasses other suitable practical chromatographic methods of separating such compounds.

The chromatographic elution characteristics of each individual hydrophobic cyclic peptide may be determined with chromatography, particularly high-performance liquid chromatography (HPLC). The HPLC data is useful for precise detection and quantification of individual hydrophobic cyclic peptides. Those skilled in these arts would understand that other types of chromatography exemplified by silica gel column chromatography and reverse-phase chromatography, may also be used.

The present methods enable recovery of greater amounts of hydrophobic cyclic peptides than those of the methods currently available. For example, a comparison of the BAH process with an exemplary method of the present invention showed that the Brühl process recovered 55 mg of a crude peptides fraction from 100 g of flaxseed oil, from which was separated 11 mg of cyclolinopeptide E. In comparison, the exemplary present method enabled recovery of 146 mg of crude peptide from 100 g of flaxseed oil, from which 16.7 mg of cyclolinopeptide E was recovered, which was 51% more than was recovered by the Brühl process. Additionally, the following hydrophobic cyclic peptides were also separated and purified: (i) 20.3 mg of cyclolinopeptide A; (ii) 16.3 mg of cyclolinopeptide C; (iii) 3.3 mg of cyclolinopeptide D; (iv) 16.7 mg of cyclolinopeptide E; (v) 1.0 mg of cyclolinopeptide F; and (vi) 6.1 mg of cyclolinopeptide G.

Another exemplary embodiment of the present invention relates to therapeutic applications for the individual cyclolinopeptides separated by the present methods. More specifically, the present invention relates to the use of the separated hydrophobic cyclic peptides for the treatment of those diseases related to the regulation of apoptosis. It is within the scope of the present invention to screen individual cyclolinopeptides and other cyclic peptides recoverable with the methods of the present invention, for their modulating effects on the expression of selected genes, particularly those involved in apoptosis. Some embodiments of the present invention relate to the use of selected individual cyclolinopeptides separated and purified according to the methods disclosed herein, for modulating at least one of three specific genes integral to apoptosis, i.e., tumor necrosis factor alpha ("P21"), p53 upregulated modulator of apoptosis ("PUMA") and BCL-2 alpha. P21 is a signalling molecule or cytokine involved in systemic inflammation and is a member of a group of cytokines that stimulate the acute-phase reaction. The primary role of P21 is in the regulation of immune cells, but it is also able to induce apoptotic cell death, to induce inflammation and to inhibit tumorigenesis and viral replication. Dysregulation and, in particular, overproduction of P21 has been implicated in a variety of human diseases, including cancer. PUMA is a pro-apoptotic member of the BCL-2 protein family. BCL-2 family members can form hetero- or homodimers, and they act as anti- or pro-apoptotic regulators that are involved in a wide variety of cellular activities. The expression of PUMA is regulated by the tumor suppressor p53, and PUMA has been shown to be involved in p53-mediated apoptosis. BCL-2 alpha, or B-cell lymphoma 2, is known as an oncoprotein and anti-apoptotic member of the BCL-2 family that prolongs the lifespan of a variety of cell types by interfering with programmed cell death. Overexpression of BCL-2 alpha induces cell proliferation and cancer. Identification of genes that are up- or down-regulated by the presence of individual cyclic peptides will be particularly useful for those diseases that are related to a de-regulation of apoptosis, such as neurodegenerative diseases, haematologic diseases, AIDs, viral infections, inflammatory diseases, autoimmune diseases, cancer and tissue damage.

Some of the examples disclosed herein relate to methods for extracting oil from plant material. Those skilled in these arts will understand that the extraction of oil from plant materials, such as flax seeds, concomitantly results in the extraction of hydrophobic peptides in the extracted oil.

Example 1

Extraction of Flax Seed Oil and Peptides from Flax Seed with a Laboratory Expeller Press Flax seeds were pressed with a Komet® expeller press (type CA 59 G3; Komet is a registered trademark of IGB Monforts Oekotec GmbH & Co., Germany) to release the oil. The flaxseed oil was filtered using a Buchner funnel filter and Whatman® #4 filter paper (Whatman is a registered trademark of Whatman International Ltd., Maidstone, Kent, UK) to remove fines (also known as "foots") from the freshly pressed oil. The filtered oil was placed under vacuum to reduce the rate of oxidation.

Example 2

Extraction of Flax Seed and Peptides in Flax Seed with Hexane

About 5 g of flax seeds were ground using a coffee grinder to produce a meal. The meal was placed in a fat extractor thimble in a beaker, to which was added about approximately 40 to 50 milliliters of hexane. The beakers were connected to a Goldfisch extractor (Model 22166, Labconco Corp., Kansas City, Mo., 64132, USA) for extraction of oil. The samples were allowed to reflux for five hours. The solvent was recovered using recovery thimbles, leaving oil in the beaker. The oil content of the seed was approximately 40% and pressed meal was found to be around 12%.

Example 3

Extraction of Flax Seed Oil and Peptides from Flax Seed with a Two-Stage Expeller Press Whole flax seed was introduced to a commercial oilseed expeller press at a rate of 24 metric tons per day. Oil coming from this type of press process is described as cold-pressed oil. The meal produced by this press treatment contained approximately 20% oil. The meal was passed through a high-velocity commercial extruder at a rate of 19 tons per day. The high friction action of the extruder caused the meal to heat to approximately 110° C. Meal exiting the extruder was passed through a conditioning screw after which it was introduced to a second expeller press. The second press reduced the oil content of the meal from 20% to approximately 9% to 10%. Oil arising from the first and second pressing of the flax seed was analyzed to determine the content of cyclolinopeptides.

The following examples disclosed herein relate to methods used for the extraction and recovery of hydrophobic peptides from the oil extracted from flax seed, as disclosed above. The present invention teaches the use of sequential washing to elute certain hydrophobic peptides into certain fractions in order to avoid the expensive and sometimes problematic use of chromatographic separation of all hydrophobic peptides loaded onto silica.

Example 4

Separation of Cyclolinopeptides from Flax Oil by Adsorption on Silica-Column Chromatography Flax oil (700 mL) diluted with 5% ethyl acetate ("EtOAc") in hexane (700 mL) was loaded on the silica-gel column (50 g), and eluted successively with 10% (v/v) EtOAc in hexane (300 mL; fraction 1), 50% (v/v) EtOAc in hexane (300 mL; fraction 2), 100% EtOAc (200 mL; fraction 3), 10% methanol ("MeOH") in dichloromethane ("DCM") (300 mL; fraction 4) and 20% MeOH in DCM (200 mL; fraction 5). After each elution step, solvents were collected and evaporated. A portion of solvent-free extract was dissolved in deuterated chloroform ("CDCl3") and used for proton nuclear magnetic resonance ("NMR") analysis. The solvent-free residue of each portion was dissolved in the same amount of acetonitrile (10 mL) and 5 microliters of each were injected onto an HPLC column (HPLC Agilent 1200 series; Column Type: ZORBAX Eclipse XDB-C18 (Reverse Phase column) Column Size: 4.6 Å-150 mm, (5 μm particle size). The chromatography conditions were: Column Flow: 0.500 ml/min; Solvent A: 70.0% (Water); Solvent B: 30.0% (Acetonitrile)

| Solvent B Timetable: | | |
|---|---|---|
| Time | Solvent B | Flow rate |
| 0 | 30 | 0.5 |
| 5 | 30 | 0.5 |
| 50 | 60 | 0.5 |
| 60 | 100 | 0.5 |
| 70 | 30 | 0.5 |
| 75 | 30 | 0.5 |

The presence of NMR spectral peaks from fraction 4 (FIG. 1) indicated the presence of enriched peptides (1.74 g). Smaller amounts of peptides were observed in fraction 3 and fraction 5. The yield of peptide is almost 2 orders of magnitude higher than by current processes known to those skilled in these arts.

Example 5

Phospholipids Removal from Fraction Four

Figure 2:
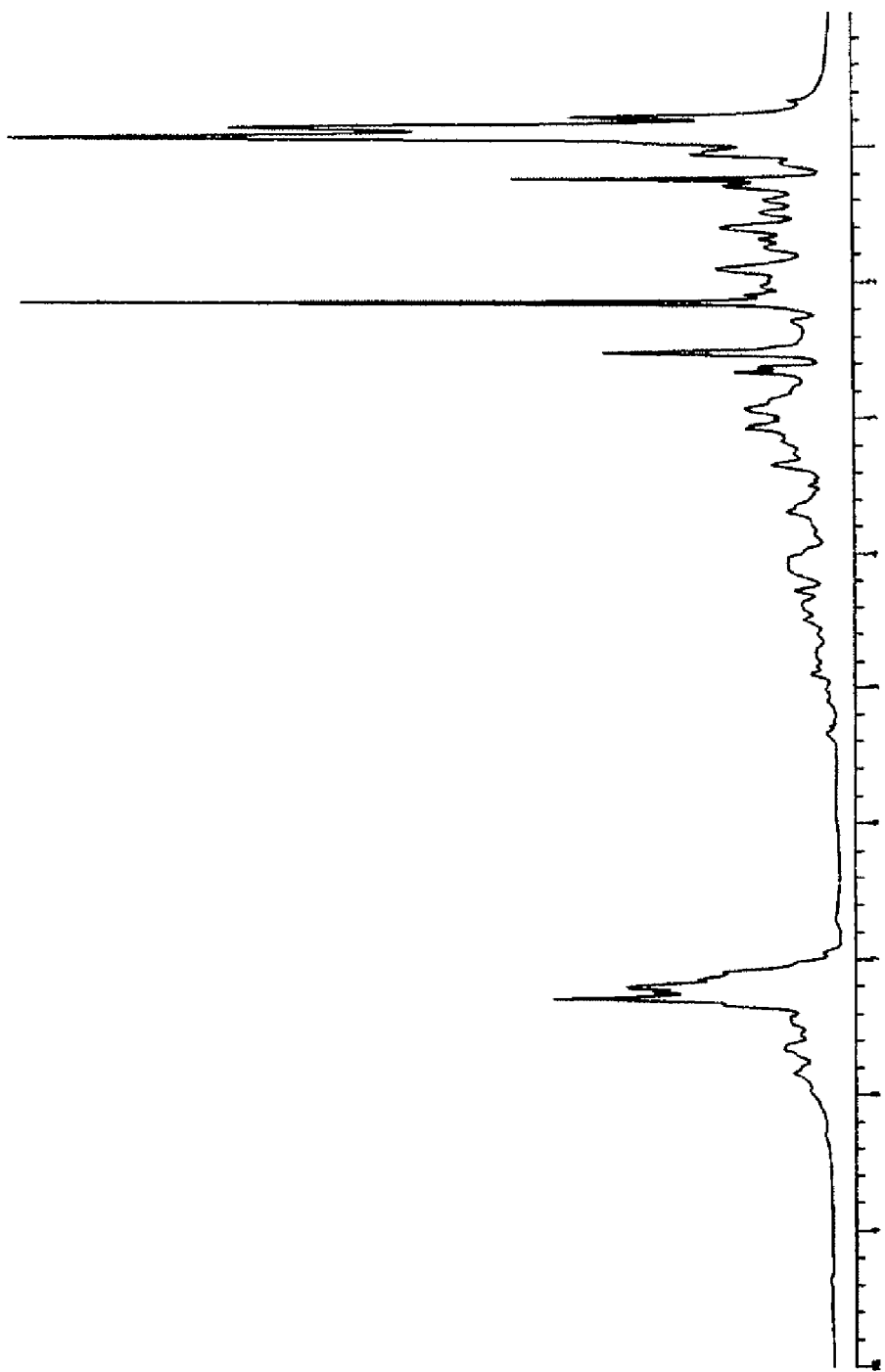
FIG. 2 is a NMR spectroscopy chart of cyclolinopeptides extracted from a non-polar fraction separated from flaxseed oil. The cyclolinopeptides were separated by elution from a silica chromatography column according to an embodiment of the present invention.

Fraction 4 (1.74 g) from Example 4, was dissolved in acetone and stirred for 30 minutes thereby forming a precipitate. The precipitate was removed by filtration and rinsed with acetone, after which each of the precipitate and mother liquor were concentrated under vacuum and prepared for proton NMR analysis. The low acetone solubility, high polarity and NMR spectrum revealed that the precipitates were phospholipids. Highly enriched peptides (1.23 g) were recovered from the mother liquor and subsequently purified by silica-gel chromatography. They were eluted successively with 100% acetone (fraction 4A), 10% MeOH in acetone (fraction 4B) and 20% MeOH in acetone (fraction 4C). Proton NMR results shown in FIG. 2 indicate that all fractions have high peptide contents (FIG. 2). The highest peptide content was observed in the third acetone fraction.

Example 6

Figure 3:
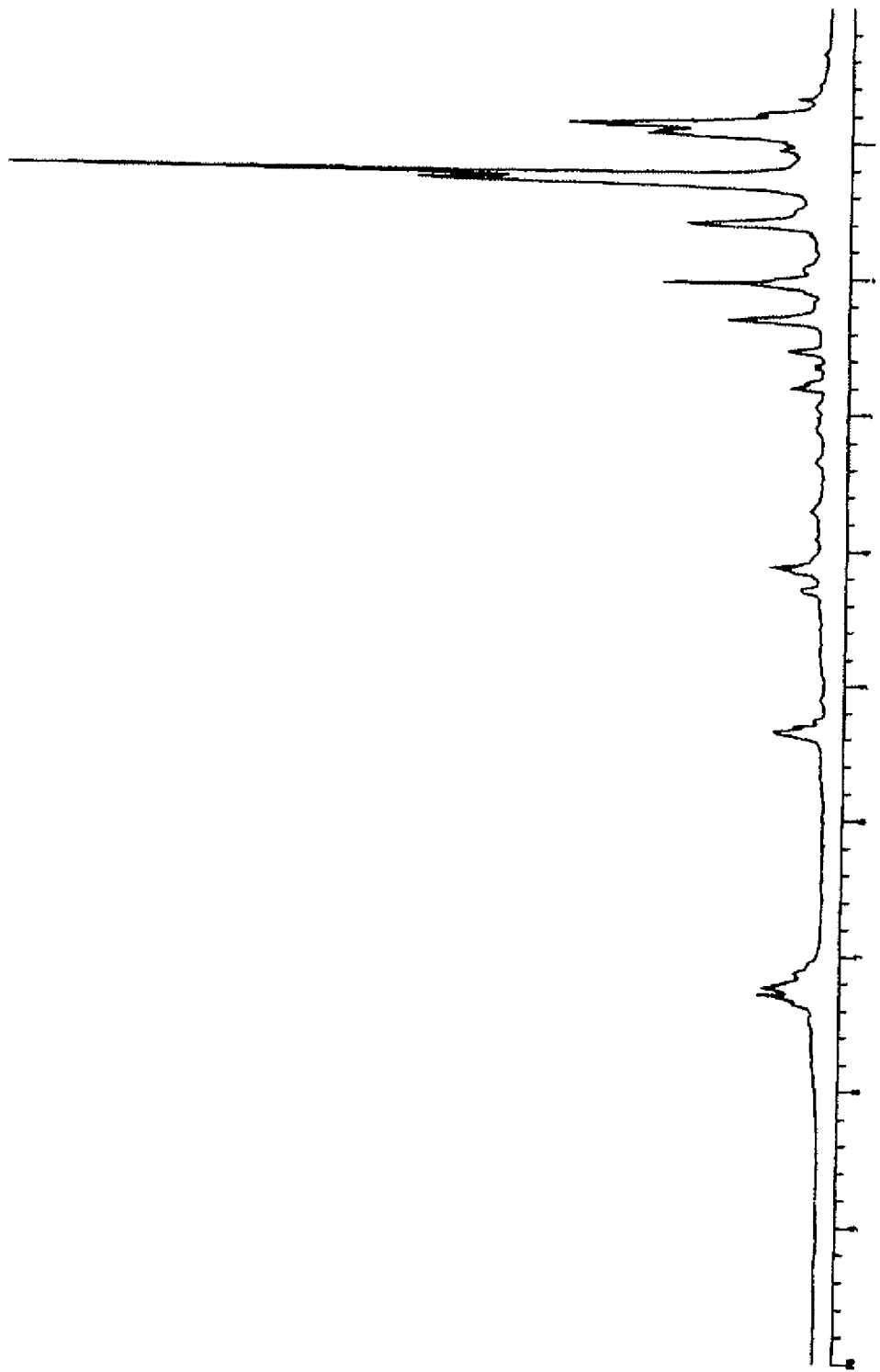
FIG. 3 is a NMR spectroscopy chart of cyclolinopeptides extracted from flaxseed oil and separated by elution from a silica chromatography column according to another embodiment of the present invention.

Maximum Recovery of Cyclolinopeptides from Flax Oil by Silica-Column Chromatography Flax oil (800 mL) diluted with 5% EtOAc in hexane (800 mL) was loaded on the silica-gel column (100 g), and eluted successively with 10% (v/v) EtOAc in hexane (1 L; fraction 1), 50% (v/v) EtOAc in hexane (1 L; fraction 2), 100% EtOAc (1 L; fraction 3) and 10% MeOH in DCM (1 L; fraction 4). Using proton NMR analysis, fractions 3 and 4 were found to consist of highly enriched peptides (686 mg and 1.686 g, respectively) (FIG. 3). The total mass of recovered peptides was 2.312 g from 800 mL flax oil.

Example 7

Figure 4:
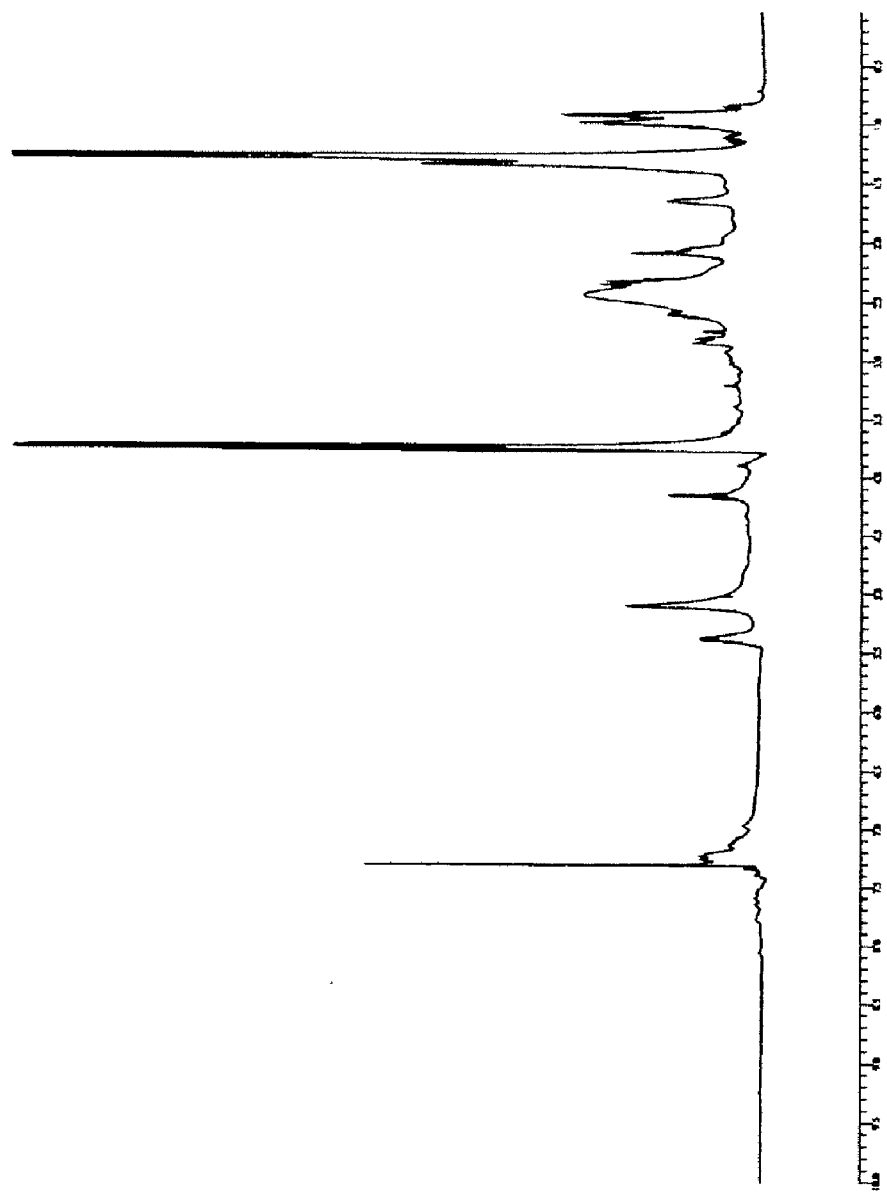
FIG. 4 is a NMR spectroscopy chart of cyclolinopeptides extracted by adsorption to silica that was intermixed into flaxseed oil and then recovered from the silica according to another embodiment of the present invention. The cyclolinopeptides were separated by elution from a silica chromatography column.

Scaling Up the Recovery of Cyclolinopeptides from Flax Oil by Silica-Column Chromatography Trysil (40 kg, W.R. Grace Corporation) was added to flax oil (2,000 L) and the mixture was agitated at 60° C. for 2 hours and then filtered to recover the silica. The mass of oil-laden silica was 78 kg. Filtered Trysil was stored in pails for further extraction. The filtered flax oil (1,960 L) was shown to be free of peptides by MALDI-MS. The solids from filtration (250 g) were placed in a flash chromatography column, which was successively eluted with 100% hexane (4 L of hexane, fraction 1), 20% EtOAc in hexane (20:80, v:v, 4 L total, fraction 2), and 100% ethanol (4 L of ethanol, fraction 3). It was found that fraction 3 (20 g) was rich in cyclic peptides (FIG. 4). By extrapolation of the recovery of 78 kg of oil-laden silica from 2,000 L, the entire fraction would yield 6.4 kg of peptide-rich material and 3.0 kg of pure peptide.

Example 8

Isolation of Individual Cyclolinopeptides

Figure 5:
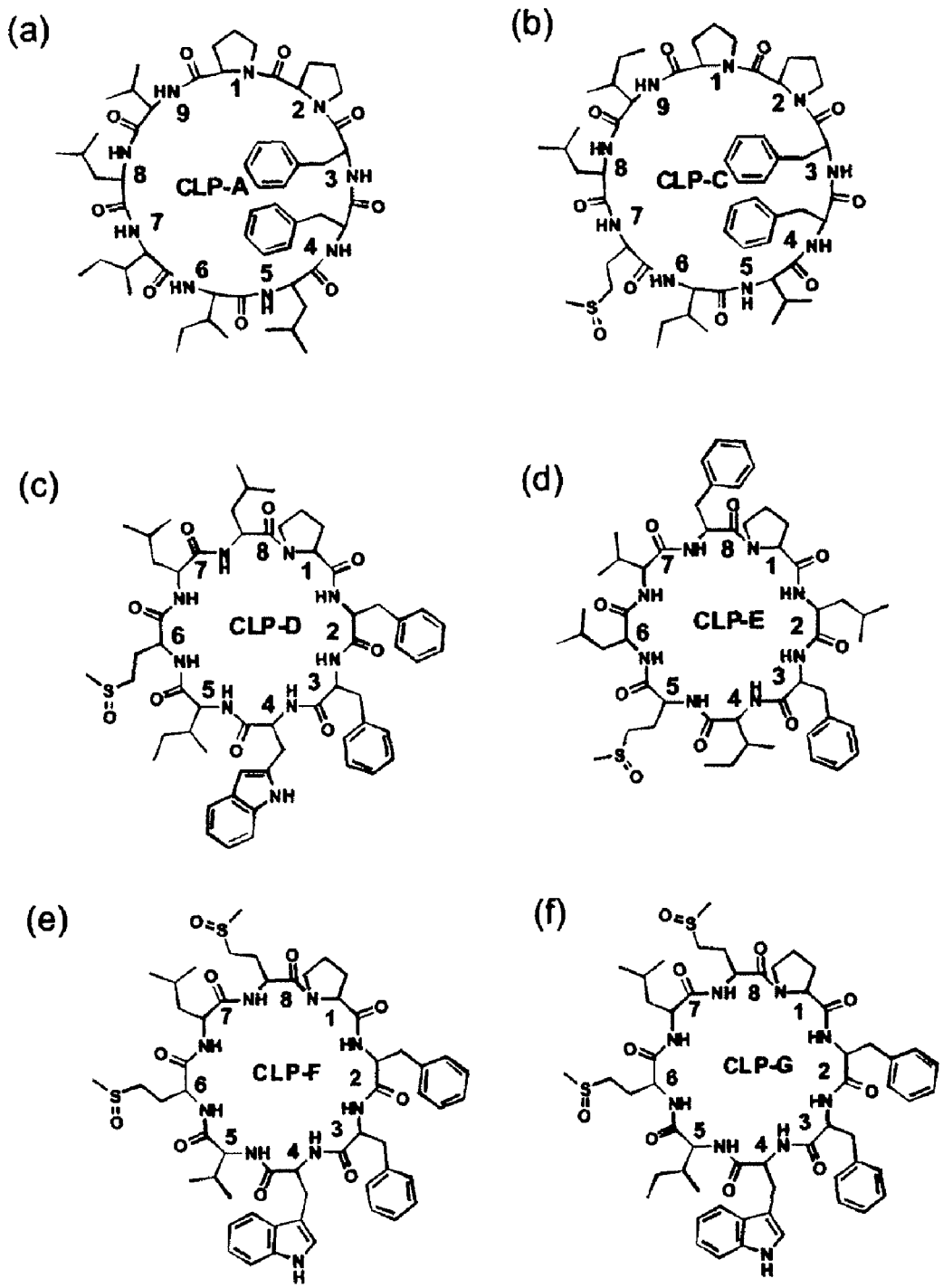
FIG. 5 shows the chemical structures of: (a) cyclolinopeptide A, (b) cyclolinopeptide C, (c) cyclolinopeptide D, (d) cyclolinopeptide E, (e), cyclolinopeptide F, and (f) cyclolinopeptide G.

The recovered peptides from Example 6 were further separated by HPLC on a 250×30 mm, 10 μm, Prep-ODS column connected to a UV/Vis detector operating at a wavelength of 254 nm. Chromatography was performed starting with a mixture of acetonitrile ("ACN") in water (30:70, v:v) and then increasing the ACN to 65% within 120 min. The mass spectra and proton NMR results revealed six cyclic peptides: cyclolinopeptide F (43% ACN; MW 1084.46); cyclolinopeptide G (44.1% ACN; MW 1098.49); cyclolinopeptide C (45.4% ACN; MW 1074.57); cyclolinopeptide E (49.2% ACN; MW 977.54); cyclolinopeptide D (51.9% ACN; MW 1064.53); and cyclolinopeptide A (59.3% ACN; MW 1040.64). Different fractions were collected and freeze-dried. The amount of different cyclic peptides in 1000 mL (888 g) oil are: 180 mg cyclolinopeptide A ("CLA"); 145 mg cyclolinopeptide C ("CLC"); 29 mg cyclolinopeptide D ("CLD"); 147.5 mg cyclolinopeptide E ("CLE"); 8.5 mg cyclolinopeptide F ("CLF") and 53.5 mg cyclolinopeptide G ("CLG"). The chemical structures of these different cyclic peptides are shown in FIG. 5.

The following examples disclose a different method for extracting and recovering hydrophobic peptides from flax oil. We have determined that the non-polar fraction of flax oil contains the majority, if not all, of the cyclic peptides, and the polar fraction contains negligible amounts of cyclic peptides or no cyclic peptides. The present invention mixes the non-polar fraction of flax oil directly with silica, such mixture then loaded onto a column and sequentially washed to elute the hydrophobic peptides.

Example 9

Separation of Cyclolinopeptides from the Non-Polar Fraction of Flax Oil by Adsorption on Silica-Column Chromatography and Sequential Washing Flax oil (1 Kg) was mixed with a solution of HCl-MeOH—$H_2O$ (5:5:90; w/w) with a magnetic stirrer. The mixture was centrifuged (20 minutes, 4000 rpm @ 22° C.) to separate polar and non-polar phases. The polar fraction settled as a semisolid white cake, which was extracted with DCM (2×300 mL). The DCM fraction was concentrated under vacuum pressure, dissolved in MeOH to run high-performance liquid chromatography ("HPLC") and in CDCl3 for proton NMR analysis. The other fraction of the semisolid cake was basified with aqueous $NH_3$ (28%; pH 9) and extracted again with DCM, concentrated under vacuum pressure, dissolved in MeOH to run HPLC and in CDCl3 for proton NMR analysis. The polar fraction was shown to contain negligible amounts of cyclic peptides or no cyclic peptides.

Figure 6:
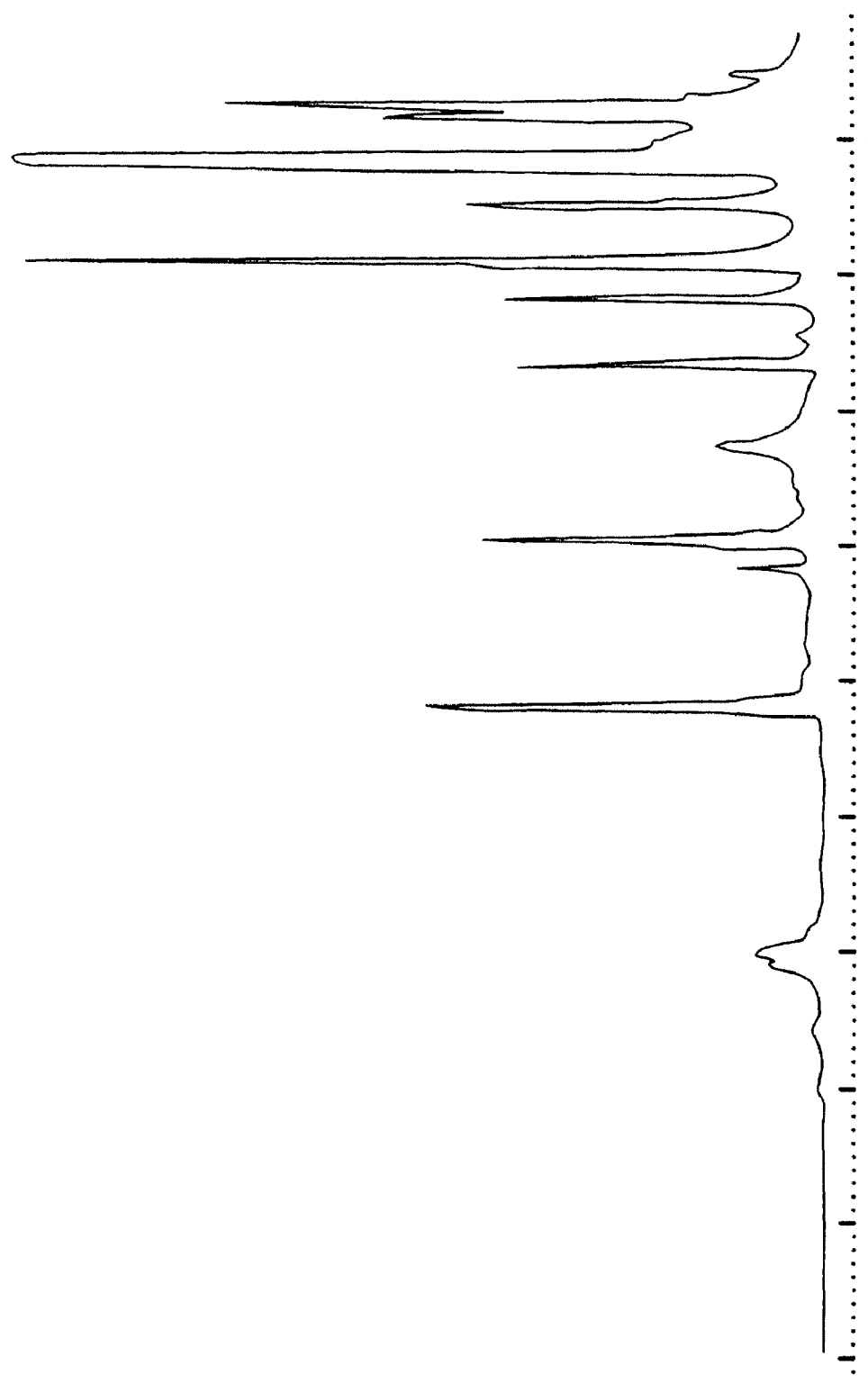
FIG. 6 comprises NMR spectroscopy charts of cyclolinopeptides extracted from a non-polar fraction separated from flaxseed oil, and separated by sequential washing and elution from a silica chromatography column according to an embodiment of the present invention: (a) is a NMR spectroscopy chart of the second fraction, (b) is a NMR spectroscopy chart of the third fraction, (c) is a NMR spectroscopy chart of the fourth fraction.
Figure 6:
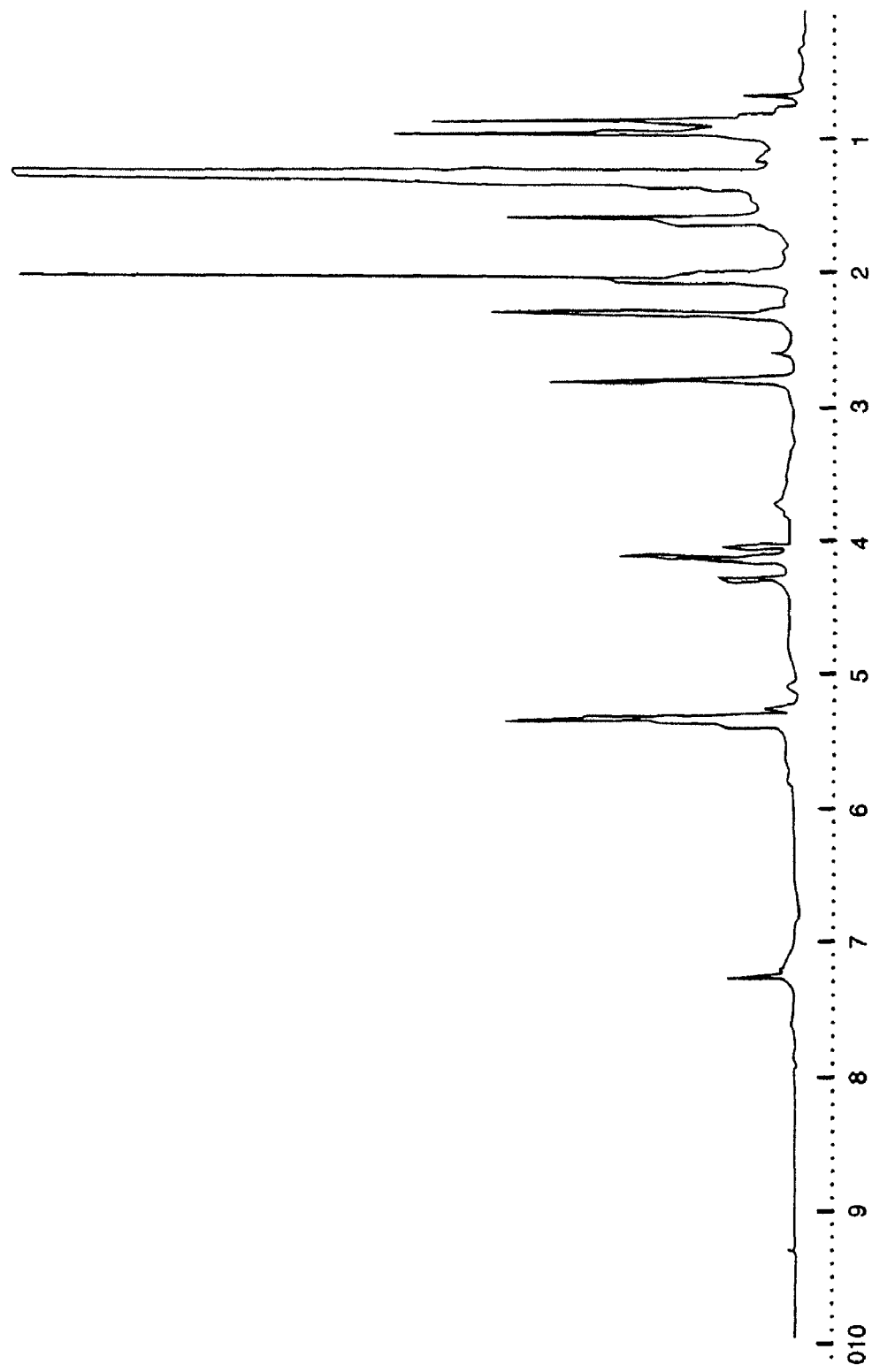

The non-polar fraction of the flax oil obtained after centrifugation was mixed with silica (50 g) with a magnetic stirrer and loaded onto the column. The oil was passed through the column and the remaining silica was first washed with hexane, eluted successively with 10% EtOAc in hexane (10:90, 300 mL, fraction 1); 20% EtOAc in hexane (20:80, 300 mL, fraction 2); 50% EtOAc in hexane (50:50, 500 mL, fraction 3); 100% EtOAc (500 mL, fraction 4) and 10% MeOH in DCM (10:90, 1000 mL, fraction 5). A portion of the solvent-free fractions was dissolved in CDCl3 for proton NMR analysis and dissolved in MeOH for running HPLC. From the spectroscopic data, it was found that fractions 2, 3 and 4 were rich in cyclic peptides (FIGS. 6(*a*), 6(*b*), 6(*c*) respectively). These fractions were subjected to further purification for separating different cyclic peptides, mainly cyclolinopeptide A.

Example 10

Separation of Cyclolinopeptides from the Non-Polar Fraction of Flax Oil by Adsorption on Silica-Column Chromatography and Sequential Washing Flax oil (1 Kg) was mixed with a solution of HCl-MeOH—$H_2O$ (5:5:90; w/w) with a magnetic stirrer. The mixture was centrifuged (20 minutes, 4000 rpm @ 22° C.) to separate polar and non-polar phases. The polar fraction settled as a semisolid white cake and was discarded since earlier spectroscopic results, as described in Example 9, showed that these fractions contain a negligible amount of cyclic peptides or no cyclic peptides.

The non-polar fraction of the flax oil obtained after centrifugation was mixed with silica (50 g) with a magnetic stirrer and loaded onto the column. The oil was passed through the column and the remaining silica was first washed with hexane (1 L) and 10% EtOAc in hexane (1 L) and then eluted successively with 20% EtOAc in hexane (20:80, 1 L, fraction 1); 50% EtOAc in hexane (50:50, 300 mL, fraction 2); 100% EtOAc (1 L, fraction 3); and 10% MeOH in DCM (10:90, 1000 mL, fraction 4).

Figure 7:
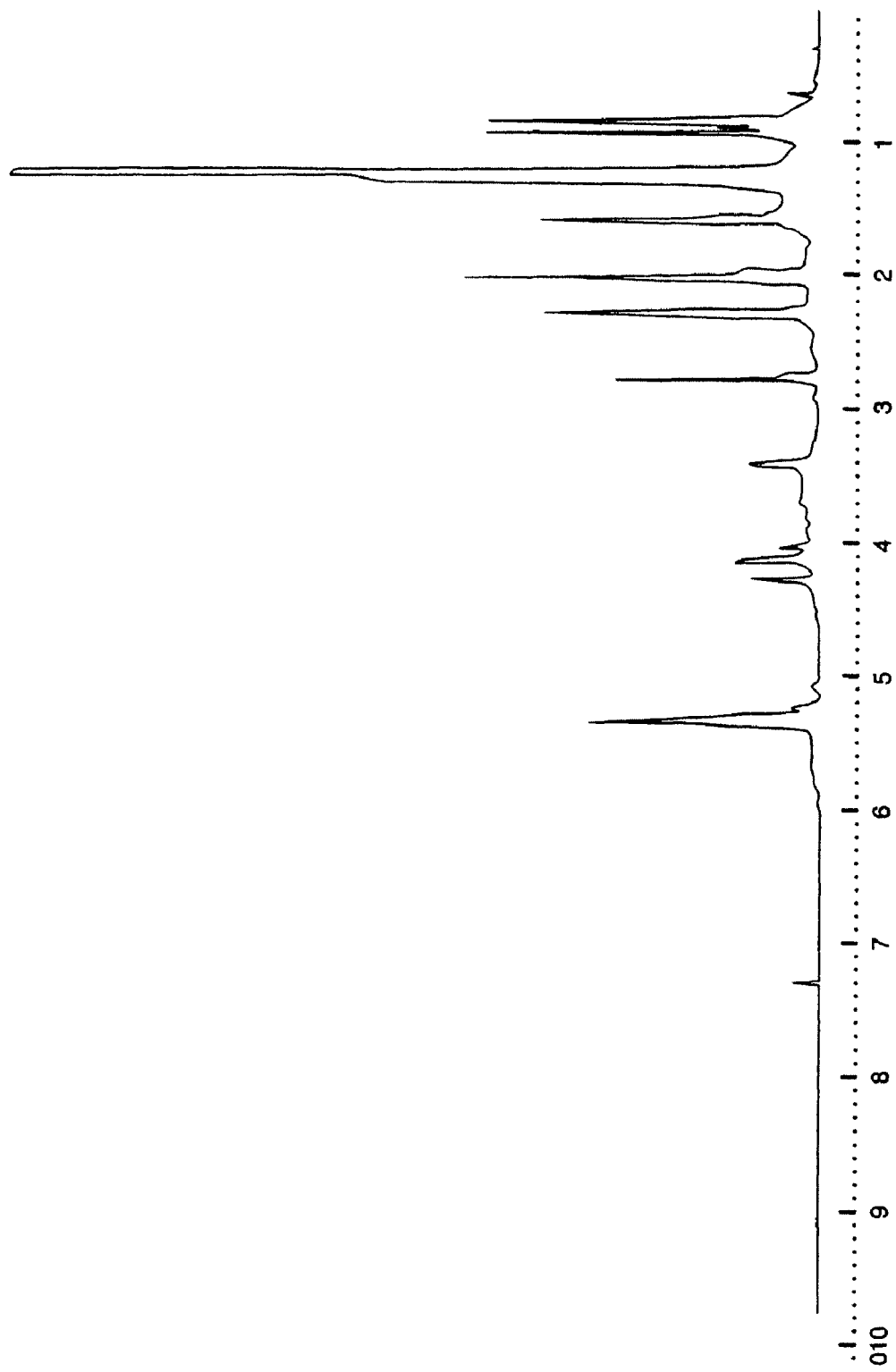
FIG. 7 comprises NMR spectroscopy charts of cyclolinopeptides extracted from a non-polar fraction separated from flaxseed oil, and separated by sequential washing and elution from a silica chromatography column according to an embodiment of the present invention: (a) is a NMR spectroscopy chart of the second fraction, (b) is a NMR spectroscopy chart of the third fraction, (c) is a NMR spectroscopy chart of the fourth fraction.
Figure 7:
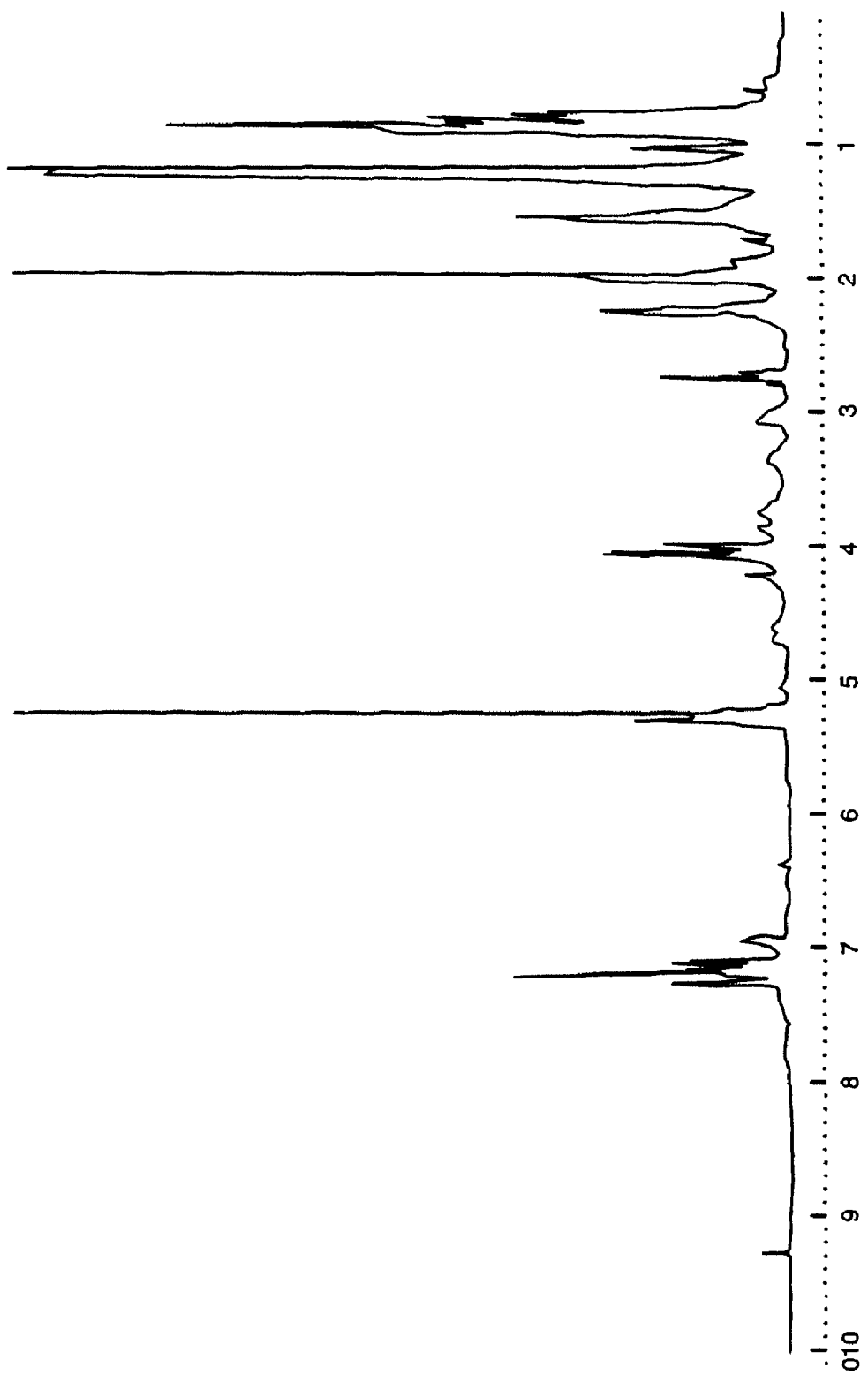
Figure 7:
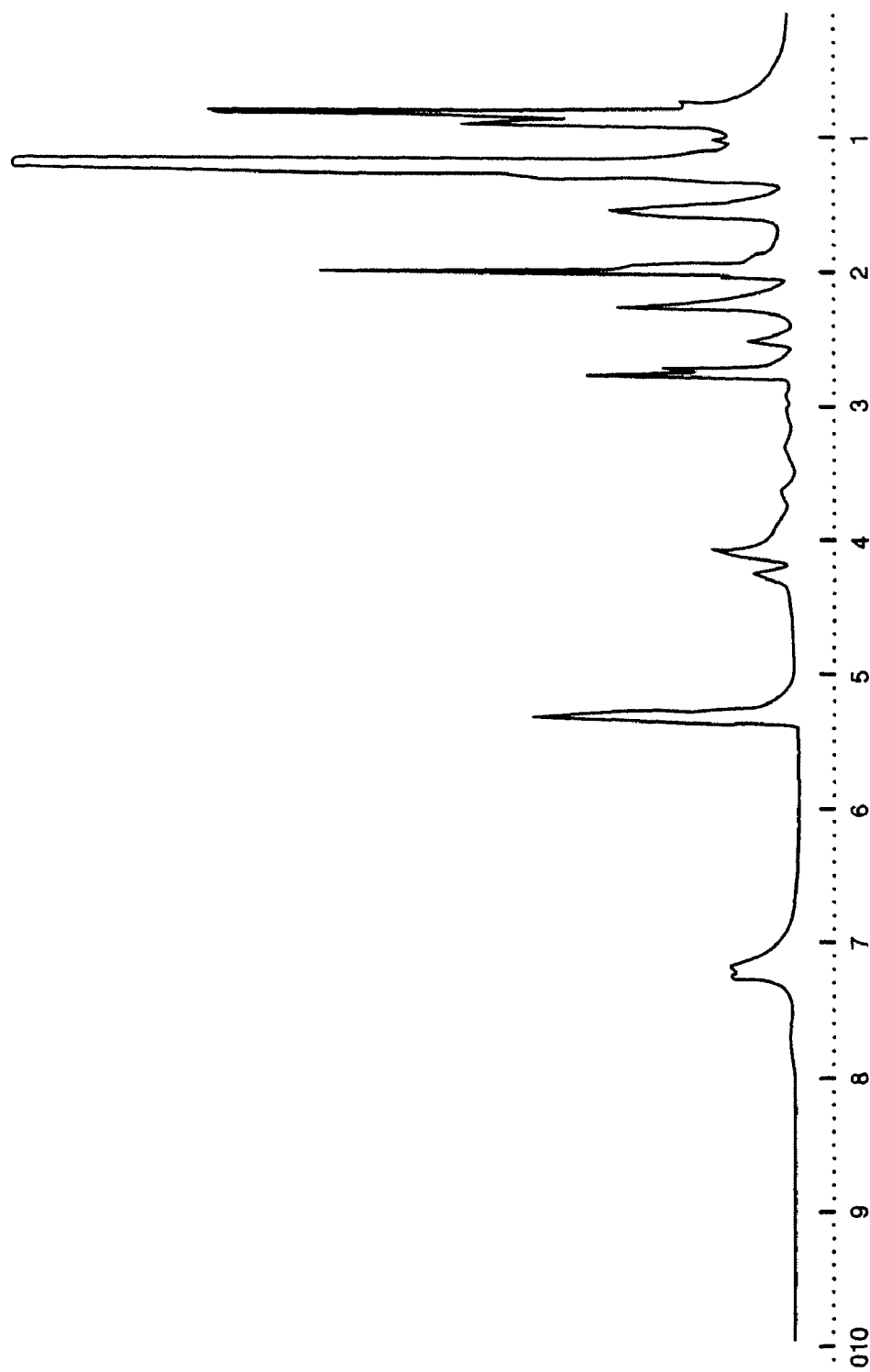

A portion of the solvent-free fractions was dissolved in CDCl3 for proton NMR analysis and dissolved in MeOH for running HPLC. From the spectroscopic data, it was found that fractions 2, 3 and 4 were rich in cyclic peptides (FIGS. 7(*a*), 7(*b*), 7(*c*) respectively). These fractions were subjected to further purification for separating different cyclic peptides, mainly cyclolinopeptide A.

Example 11

Separation of Cyclolinopeptides from the Non-Polar Fraction of Flax Oil by Adsorption on Silica-Column Chromatography and Sequential Washing Flax oil (2 Kg) was mixed with a solution of HCl-MeOH—$H_2O$ (2.5:2.5:90; w/w) with a magnetic stirrer. The mixture was centrifuged (20 minutes, 4000 rpm @ 22° C.) to separate polar and nonpolar phases. The polar fraction settled as a semisolid white cake and was discarded since earlier spectroscopic results, as described in Example 9, showed that these fractions contain a negligible amount of cyclic peptides or no cyclic peptides.

Figure 8:
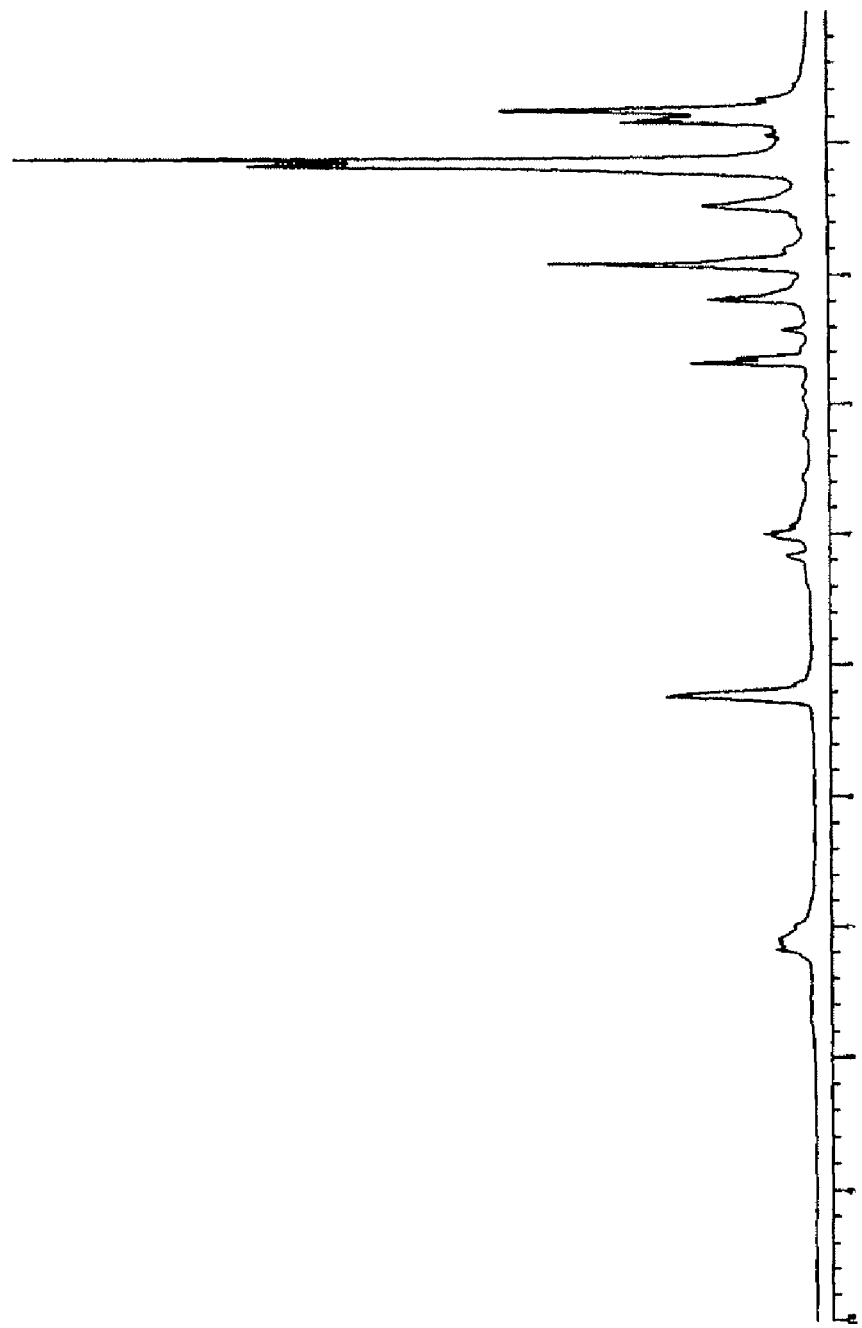
FIG. 8 is a NMR spectroscopy chart of cyclolinopeptides extracted from a non-polar fraction separated from flaxseed oil. The cyclolinopeptides were separated by sequential washing and elution from a silica chromatography column according to an embodiment of the present invention.

The non-polar fraction of the flax oil obtained after centrifugation was mixed with silica (100 g) with a magnetic stirrer and loaded onto the column. The oil was passed through the column and the remaining silica was first washed with hexane (2 L) and eluted successively with 50% EtOAc in hexane (50:50, 2 L, fraction 1); 100% EtOAc (2 L, fraction 2); and 10% MeOH in DCM (10:90, 2 L, fraction 3). A portion of the solvent-free fractions was dissolved in CDCl3 for proton NMR analysis and dissolved in methanol for running HPLC. From the spectroscopic data, it was found that fractions 2, 3 and 4 were rich in cyclic peptides (FIG. 8). These fractions were subjected to further purification for separating different cyclic peptides, mainly cyclolinopeptide A.

Example 12

Figure 9:
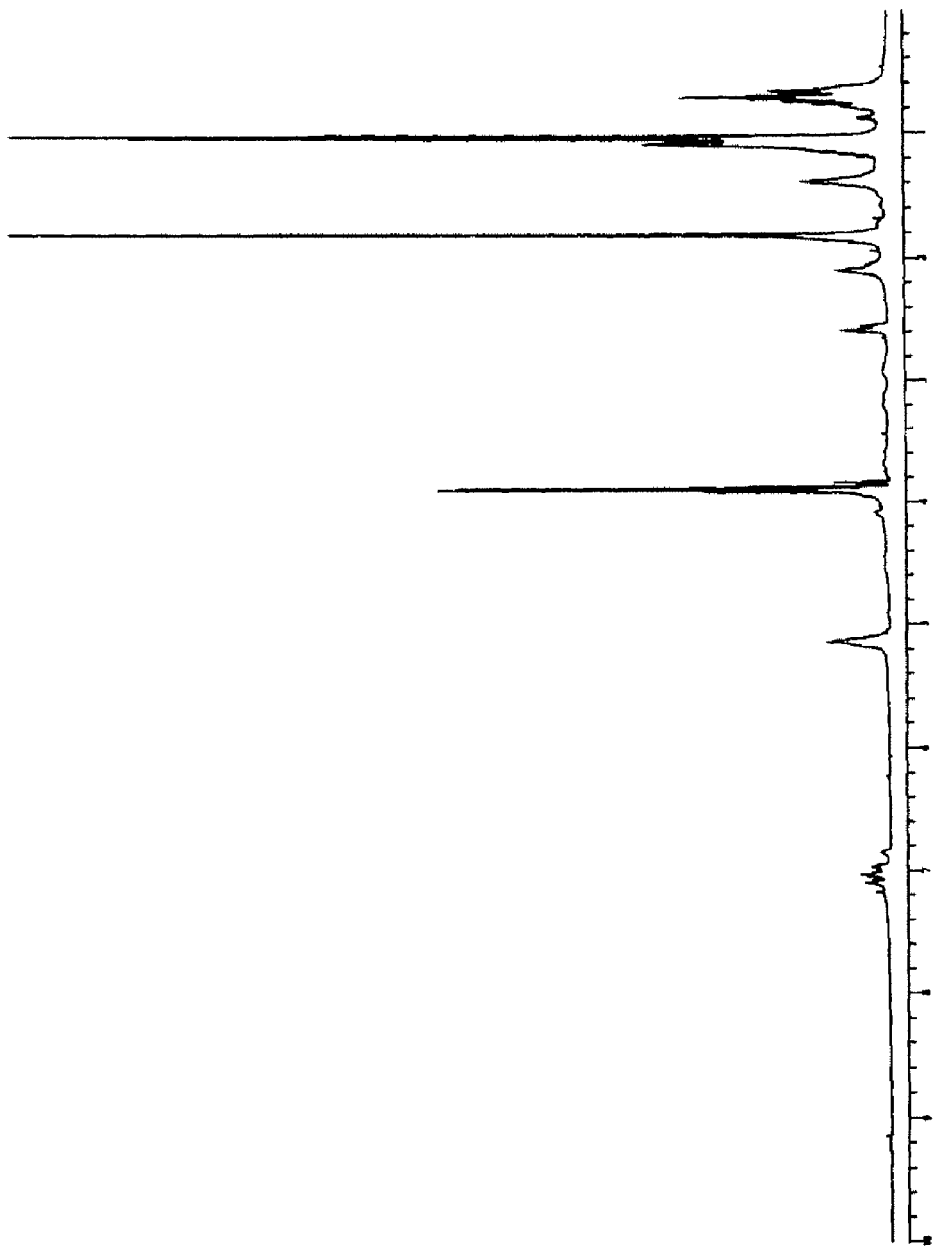
FIG. 9 is a NMR spectroscopy chart of cyclolinopeptides extracted by adsorption to silica that was intermixed into flaxseed oil and then recovered from the silica according to another embodiment of the present invention. The cyclolinopeptides were separated by elution from a silica chromatography column according to an embodiment of the present invention.

Separation of Cyclolinopeptides from Flax Oil by Adsorption on Silica-Column Chromatography and Sequential Washing Flax oil (2 Kg), without any pre-treatment, was mixed with silica (100 g) with a magnetic stirrer and loaded onto the column. The oil was passed through the column and the remaining silica was first washed with hexane (2 L) and subjected to gradient elution with EtOAc-hexane (50:50, 60:40, 70:30, 80:20, 90:10; 2 L; fraction 1); 100% EtOAc (100:0, 2 L, fraction 2); 10% MeOH in DCM (10:90, 2 L, fraction 3); and MeOH-DCM-ammonium hydroxide (20:80: 1, 1 L, fraction 4). A portion of the solvent-free fractions was dissolved in CDCl3 for proton NMR analysis and dissolved in MeOH for running HPLC. From the spectroscopic data, it was found that fractions 2 and 3 were rich in cyclic peptides (FIG. 9). These fractions were subjected to further purification for separating different cyclic peptides, mainly cyclolinopeptide A.

Example 13

Figure 10:
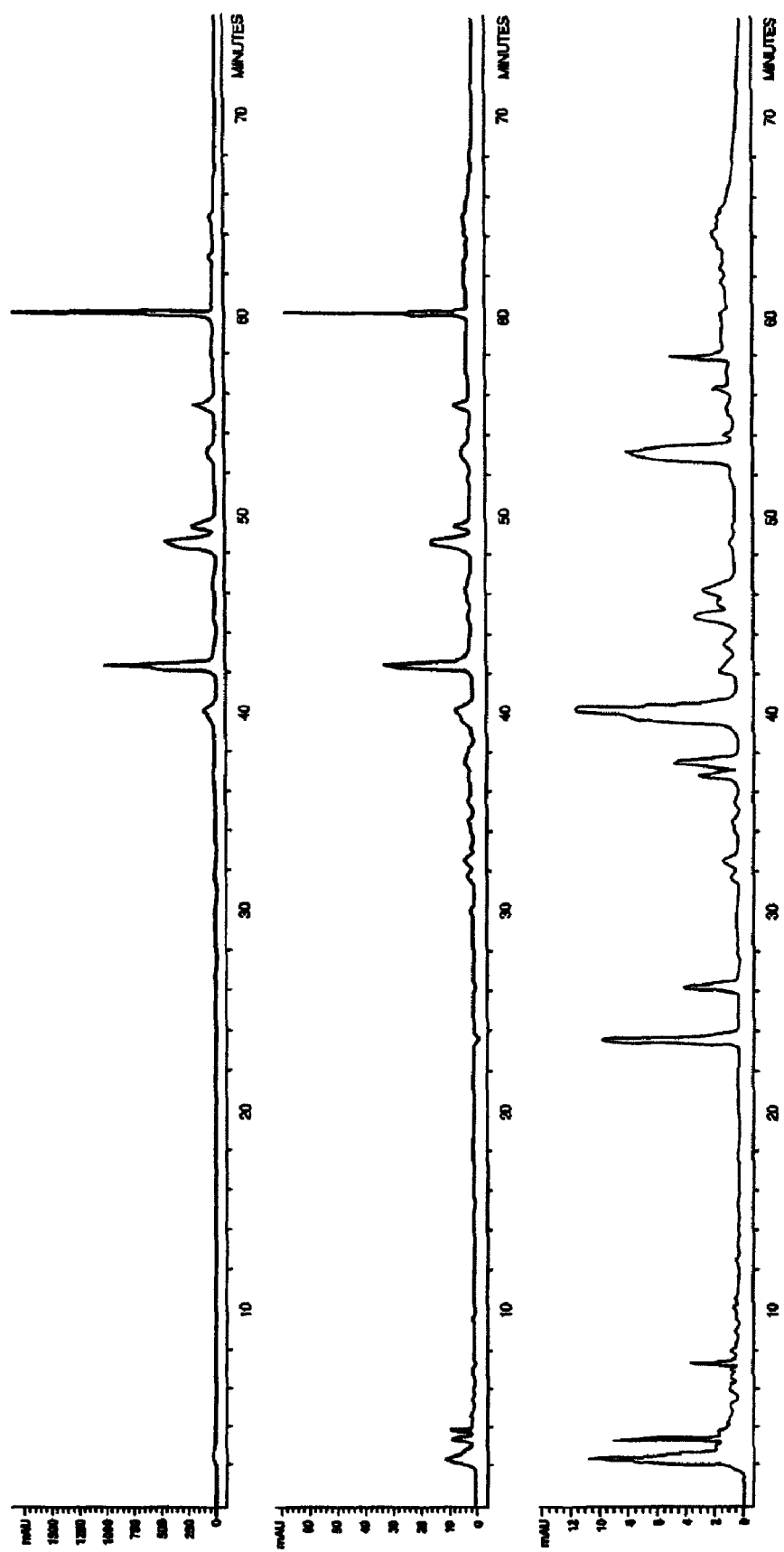
FIG. 10 comprises HPLC chromatograms of cyclolinopeptides extracted from a non-polar fraction separated from flaxseed oil. The cyclolinopeptides were separated by sequential washing and elution from a silica chromatography column according to an embodiment of the present invention: (a) is a HPLC chromatogram of the first extract, (b) is a HPLC chromatogram of the second extract, (c) is a HPLC chromatogram of the third extract.
Figure 10:
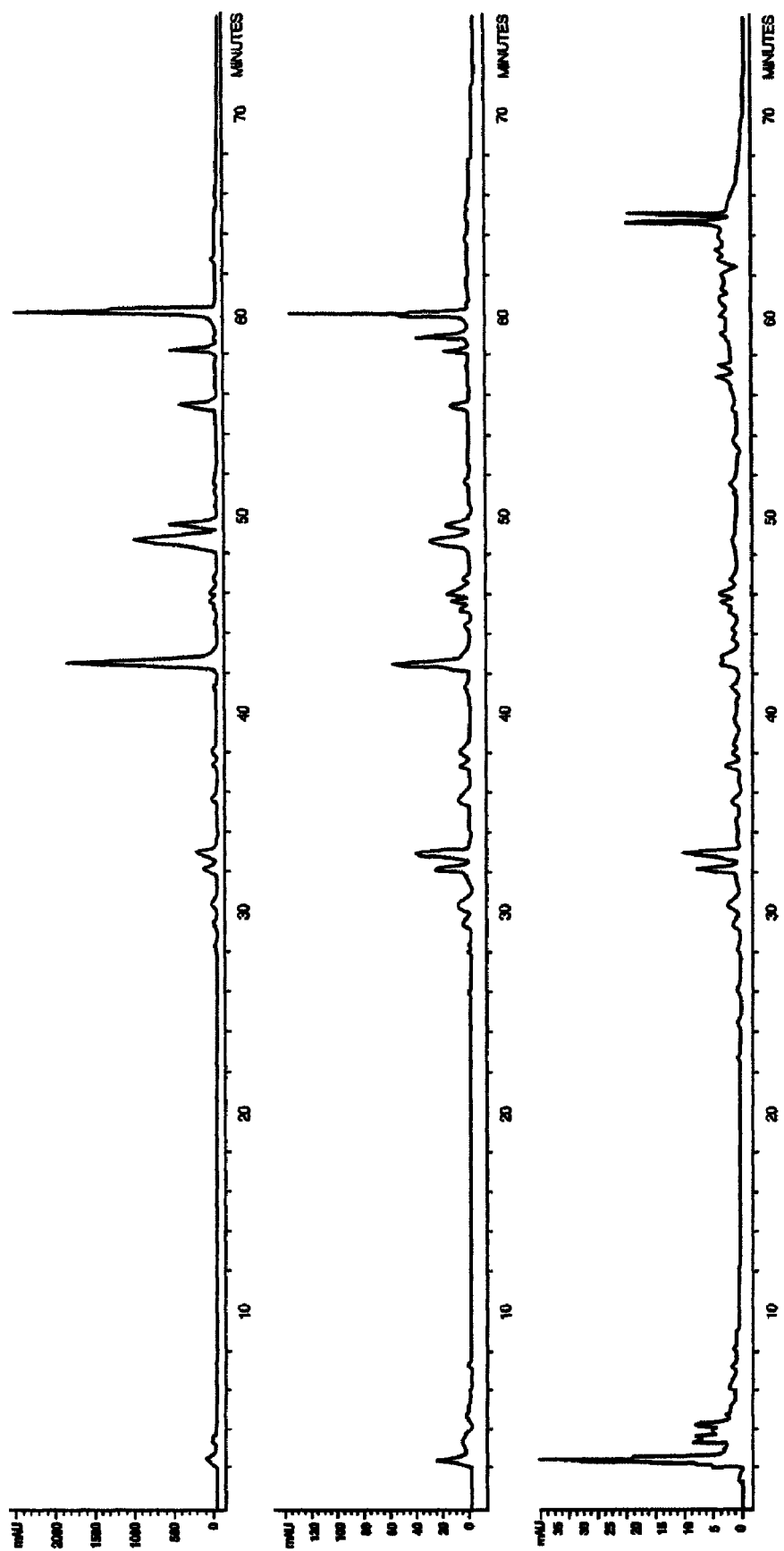
Figure 10:
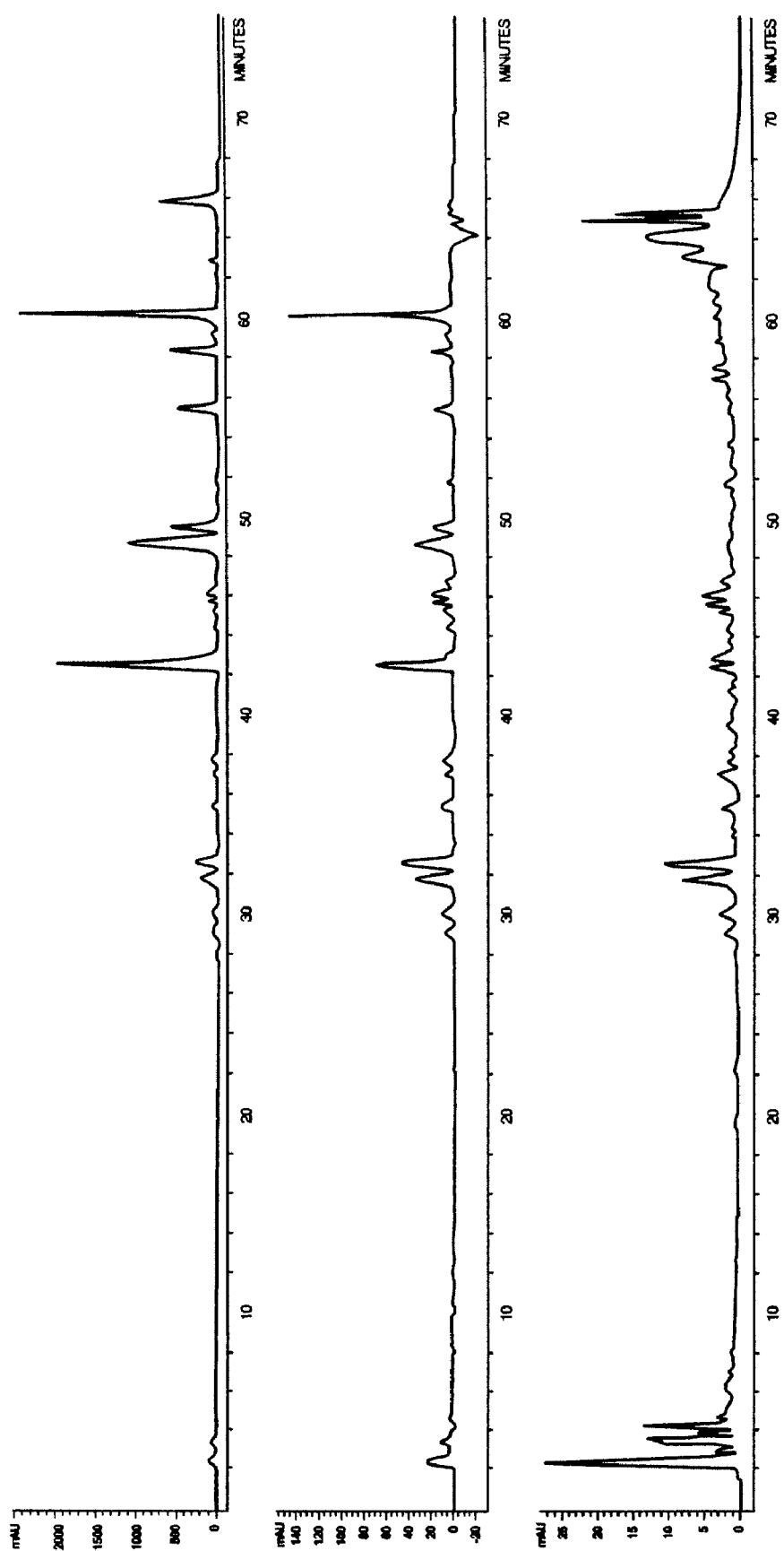
Figure 11:
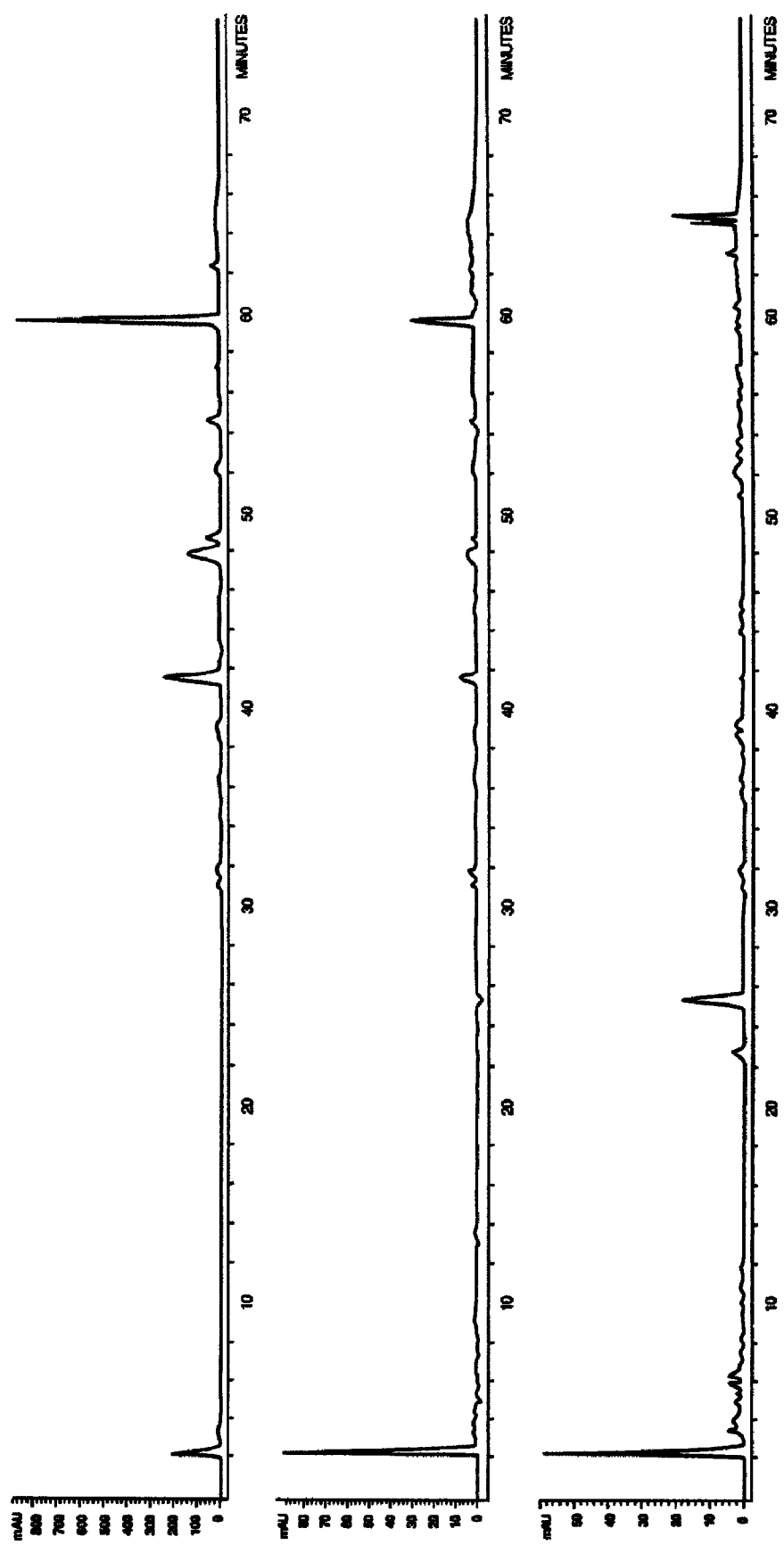
FIG. 11 comprises HPLC chromatograms of cyclolinopeptides extracted from a polar fraction separated from flaxseed oil. The cyclolinopeptides were separated by elution from a silica chromatography column according to an embodiment of the present invention: (a) is a HPLC chromatogram of the first extract, (b) is a HPLC chromatogram of the second extract, (c) is a HPLC chromatogram of the third extract.
Figure 11:
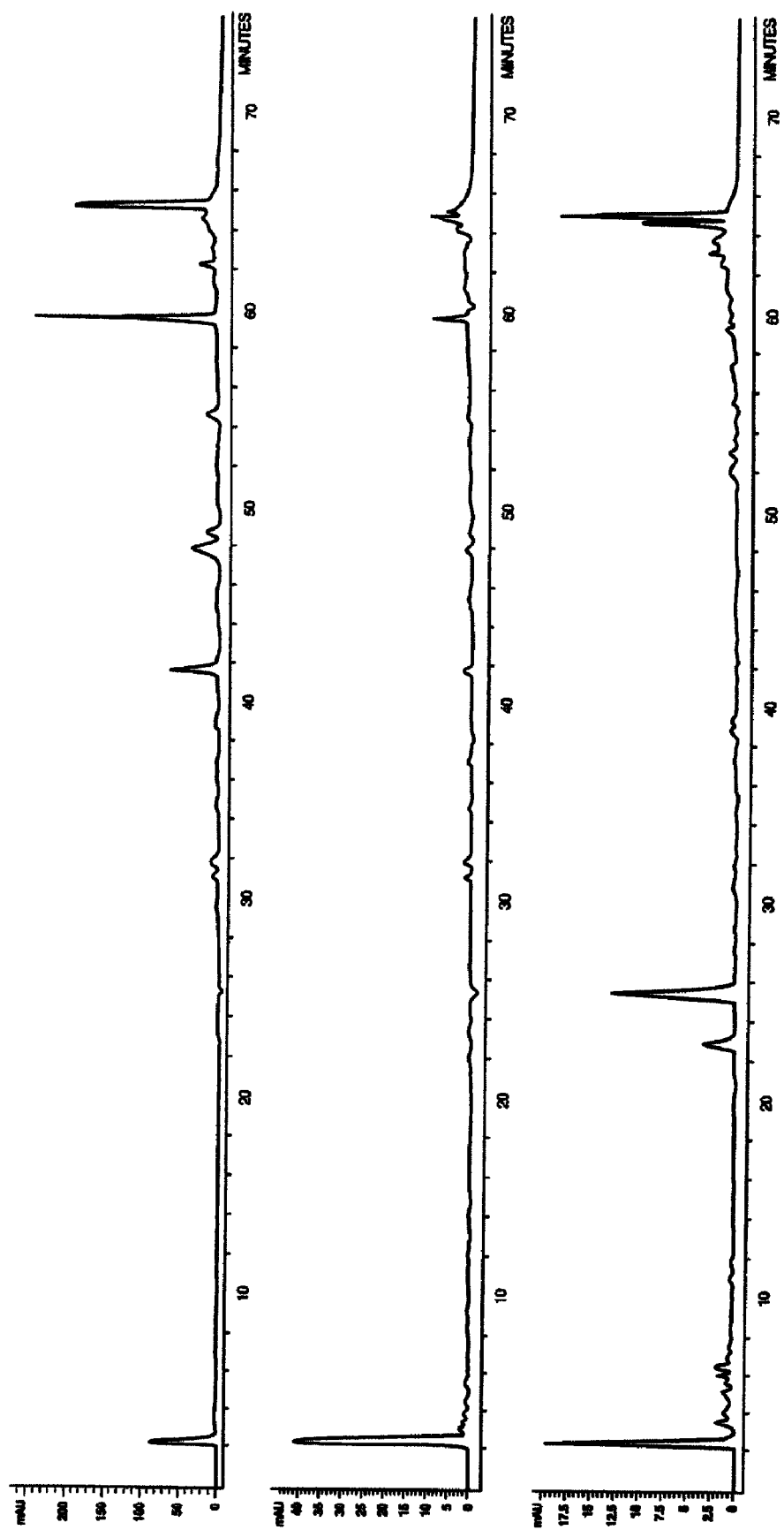
Figure 11:
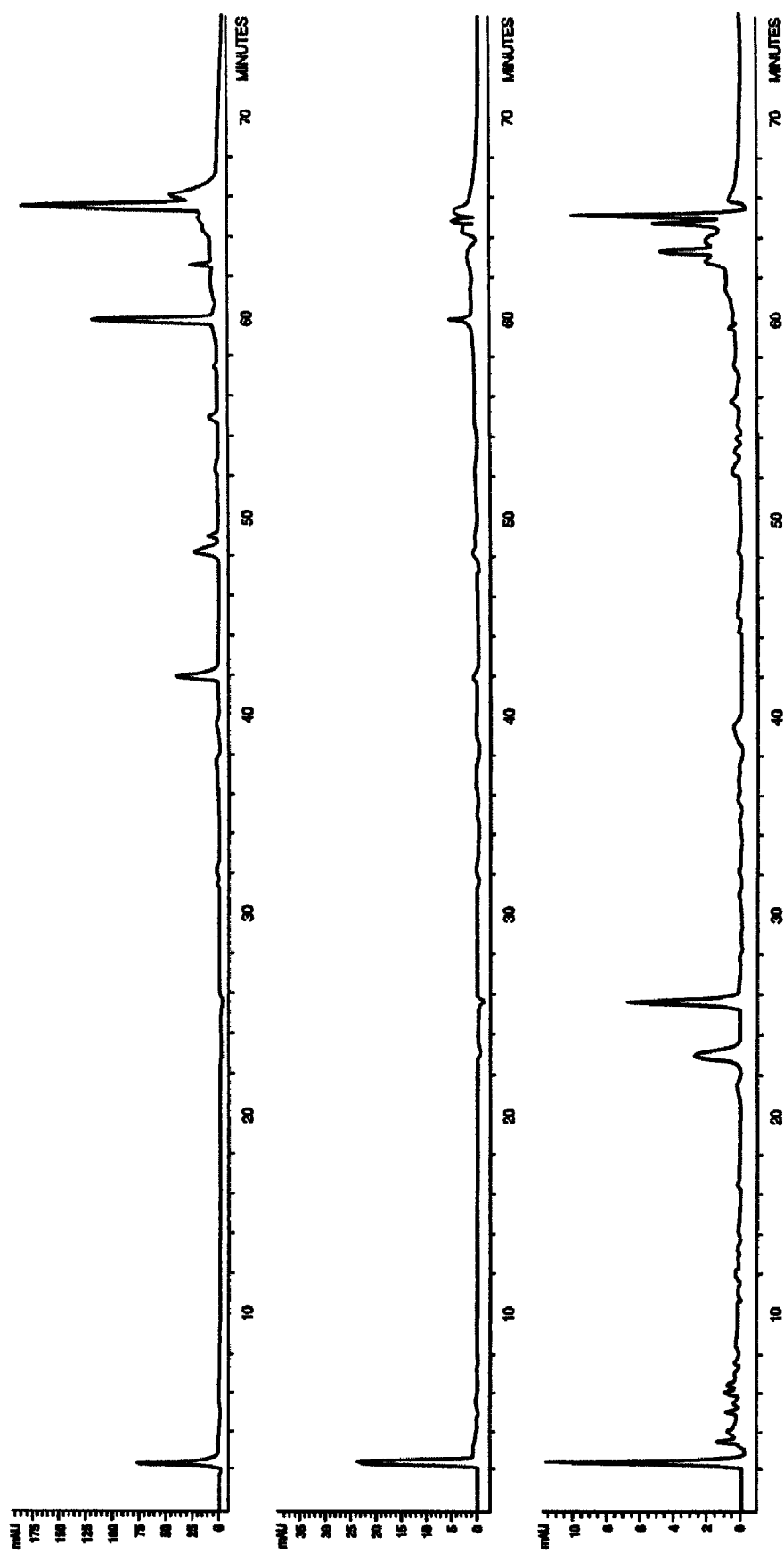

Separation of Cyclolinopeptides from Both Non-Polar and Polar Fractions of Flax Oil Flax oil (300 mL) was extracted with acidic MeOH in three parallel sets. In each, flax oil (100 mL) was shaken with a solution of HCl-MeOH (5:95; w/w) in a separatory funnel. The first set was extracted with acidic MeOH (1×100 mL), Ext.1; second set was extracted with acidic MeOH (2×100 mL), Ext.2 and third set was extracted with acidic MeOH (3×100 mL), Ext.3. Nonpolar layers were mixed with silica (5%, w/v) with a magnetic stirrer and filtered using a Buchner funnel. The remaining silica was first washed with EtOAc-hexane (20:80) and then with 100 mL of MeOH-DCM (10: 90). The filtrates were collected and solvent was removed by vacuum evaporation. The residue was dissolved in MeOH and subjected to HPLC. Ext.1, Ext.2 and Ext.3 were rich in cyclic peptides, with Ext.1 containing the highest amount (FIG. 10).

The polar fractions, Ext.1A, Ext.2A and Ext.3A were again extracted with hexane (2×100 mL) to remove residual oil. Oil-free polar fractions were subjected to HPLC to see the presence of any cyclic peptides. All fractions contained cyclic peptides, with Ext.1A containing the highest amount (FIG.

Figure 12:
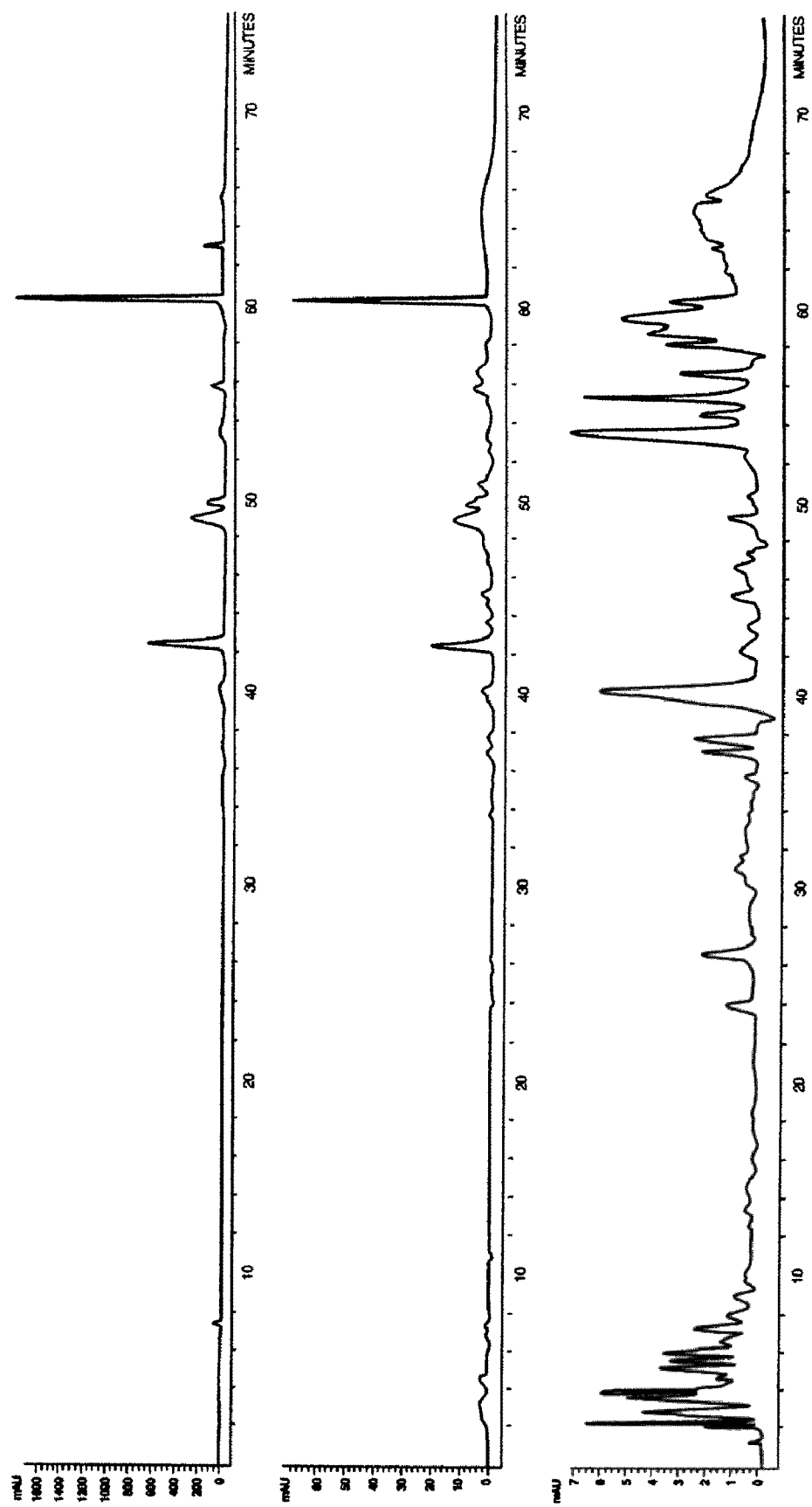
FIG. 12 is a HPLC chromatogram of cyclolinopeptides extracted from a first extract from a polar fraction separated from flaxseed oil. The cyclolinopeptides were separated by elution from a silica chromatography column according to an embodiment of the present invention.

11). Example 16: Separation of cyclolinopeptides from flax oil by adsorption to silica and sequential washing Flax oil (300 mL) was extracted with silica in three parallel sets. In each, flax oil (100 mL) was mixed with silica (5%, w/v) with a magnetic stirrer and filtered using a Buchner funnel. The remaining silica was first washed with EtOAc-hexane (20:80) and then with 100 mL of MeOH-DCM (10:90). The first set was washed with EtOAc-hexane (20:80) (1×100 mL) and then the filtrate was collected, Ext.1; the second set was washed with EtOAc-hexane (20:80) (2×100 mL) to collect Ext.2; and the third set washed with EtOAc-hexane (20:80) (3×100 mL) to get Ext.3. The filtrates collected were dried by vacuum evaporation. The residue was dissolved in acetonitrile and subjected to HPLC. Ext.1 was rich in cyclic peptides, while neither Ext.2 nor Ext.3 contained any peptides (FIG. 12).

Example 14

Simplified Purification Method for the Separation and Purification of Cyclic Peptides from Flax Oil Flax oil (100 mL) was mixed with silica (5%, w/v) in a 200 mL beaker and the mixture was stirred with a magnetic stirrer at room temperature for 30 minutes. The oil-silica solution was filtered using a Buchner funnel (Whatman® #1 filter paper diameter—65 mm). The silica in the Buchner funnel was first washed with EtOAc-Hexane (20:80) to remove vegetable oil and low polarity substances. Thereafter, the silica was repeatedly washed with solvents of increasing polarity, as described below.

In order to determine the presence of peptides in the solvent eluting from each fraction, the fractions were collected and solvent removed by vacuum evaporation. The solvent-free residue of each portion was dissolved in the same amount of acetonitrile (10 mL) and 5 µM injected onto an HPLC column (HPLC Agilent 1200 series; Column Type: ZORBAX® Eclipse XDB-C18 (Reverse Phase column); Column Size: 4.6 Å-150 mm, 5 µm particle size (ZORBAX is a registered trademark of Agilent Technologies Inc., Santa Clara, Calif., USA). In this Example and in Example 18, HPLC is used as an analytical tool to determine which peptides elute with each fraction, based on the retention times shown in Table 1, and to quantify the amount of each cyclic peptide in each fraction.

TABLE 1

| Retention time (min.) for cyclic peptide standards | | | | | |
|---|---|---|---|---|---|
| Cyclic peptides | | | | | |
| A | C | D | E | F | G |
| Retention time ($t_R$) 60.19 | 42.18 | 53.12 | 48.84 | 37.04 | 39.87 |

Example 15

Figure 13:
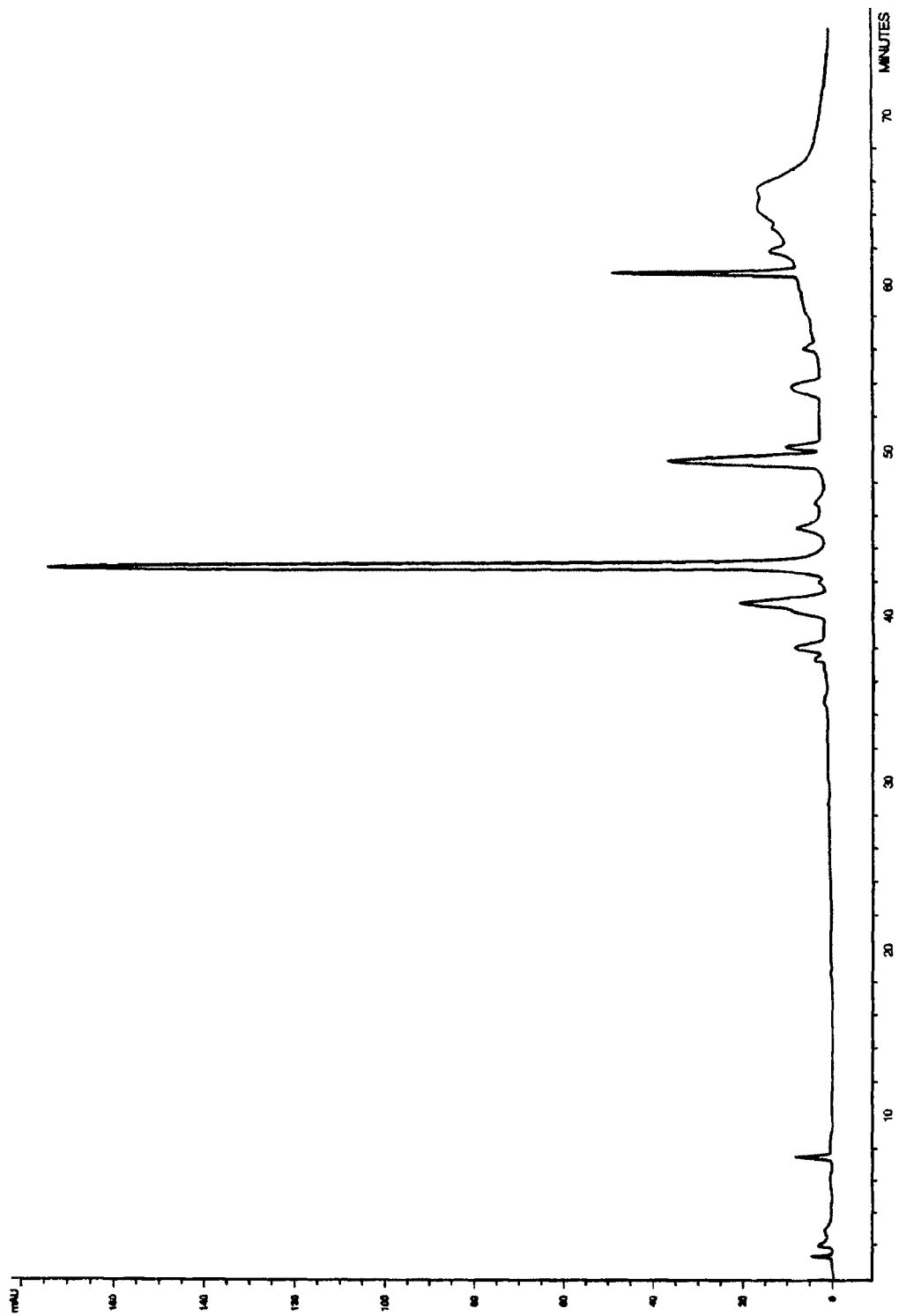
FIG. 13 comprises NMR spectroscopy charts of cyclolinopeptides extracted from a polar fraction separated from flaxseed oil, and separated by three sequential washes with 10% ethanol in ethyl acetate according to an embodiment of the present invention: (a) is a NMR spectroscopy chart of the first extract, (b) is a NMR spectroscopy chart of the second extract, (c) is a NMR spectroscopy chart of the third extract.
Figure 13:
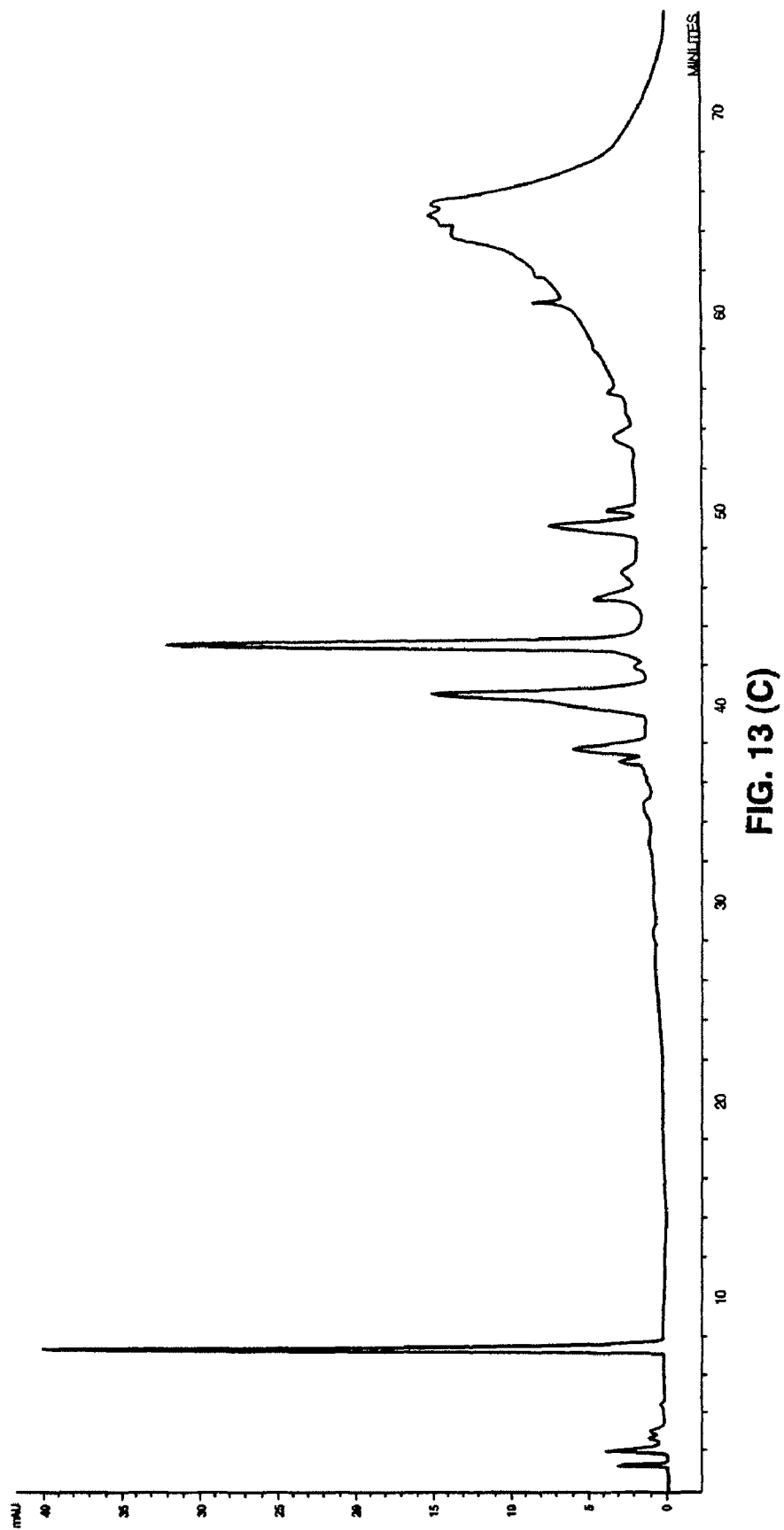

Simplified Purification Method for the Separation and Purification of Cyclic Peptides from Flax Oil Flax oil (100 mL) was mixed with silica (5%, w/v) in a 200 mL beaker and the mixture was stirred with a magnetic stirrer at room temperature for 30 minutes. The oil-silica solution was filtered using a Buchner funnel (Whatman® #1 filter paper diameter—65 mm). The silica was first washed with EtOAc-Hexane (20:80) and then with 10% EtOH in EtOAc. The first fraction of filtrate from the first wash with 20% EtOAc in hexane (100 mL) was discarded. The next fractions of filtrates were collected from successive washes with 10% EtOH in EtOAc as Ext.1 (100 mL), Ext.2 (100 mL) and Ext.3 (100 mL). The filtrates were collected and solvent was removed by vacuum evaporation. The solvent-free residue of each portion was dissolved in the same amount of acetonitrile (10 mL) and subjected to HPLC analyses, as described in Example 17, to examine extraction efficiency of cyclic peptides. From HPLC chromatograms, it was found that Ext.1 was rich in both cyclic peptide A and cyclic peptide C, while Ext.2 contained mainly cyclic peptide C (FIGS. 13(a), 13(b), 13(c), respectively). This result provides a guide for the large-scale simple purification of cyclic peptide C as well as cyclic peptide A.

Example 16

Flax Oil with Improved Polymerization Properties

Flaxseed oil was produced as described in example 1 and separated into two 1-L samples. One sample of flaxseed oil was passed through a column containing 50 g of silica gel and collected after egress from the column. The second sample was used as the control reference oil. Analysis of the egressed flaxseed oil showed that the egressed oil was free of cyclolinopeptides after the silica treatment. The viscosities of the two flaxseed oil samples were determined at 28° C. using a number three Shell cup. The two samples were placed into the Shell cups, heated to 160° C. and held at that temperature for 300 minutes, and then cooled to 28° C. After cooling, the viscosity measurements were repeated. The data showed that the viscosity of control reference oil containing cyclolinopeptides did not change after the heat treatment. However, the viscosity of the oil from which the cyclolinopeptides had been removed increased after the heat treatment. These data demonstrate that flaxseed oils containing cyclolinopeptides polymerized more slowly than flaxseed oils that have the cyclolinopeptides removed.

Example 17

Biologically Active Flax Oils with Standardized Levels of Cyclolinopeptides and/or Cyclolinopeptide Profiles The silica absorption methods disclosed herein enable: (a) the complete removal of cyclolinopeptides from flaxseeds oil, and (b) the separation, identification and quantification of individual cyclolinopeptides from the recovered fractions. Those skilled in these arts will understand that these methods can be adapted for producing flaxseed oils having standardized amounts of selected cyclolinopeptides whereby one or more of the separated and quantified cyclolinopeptides are added back into flaxseed oils from which all cyclolinopeptides were previously removed on a weight per weight basis. We have found that the precision of the analysis is greatly enhanced by the addition of an internal standard that is readily measured by mass spectrometry. In specific we have found that valinomycin is an ideal standard for the purposes of determining the cyclolinopeptides contents of flaxseed oils.

Example 18

Figure 17:
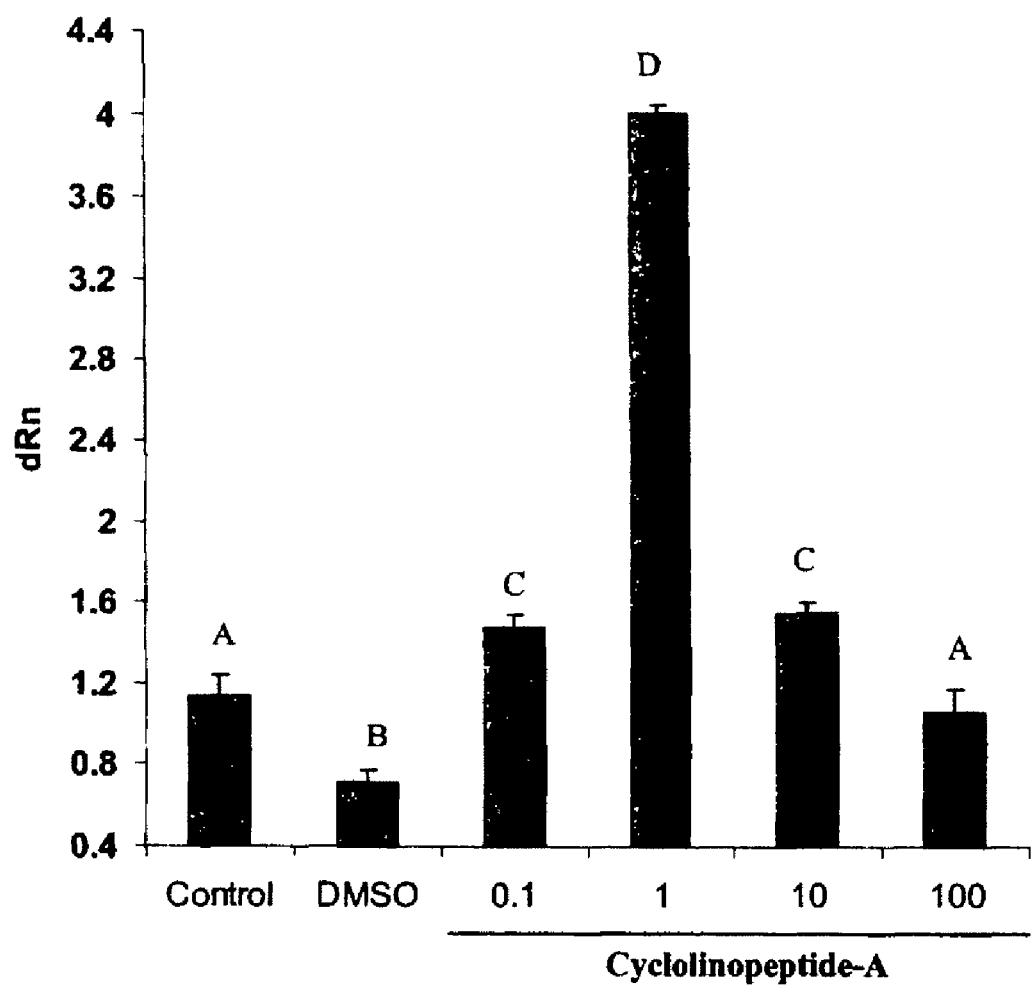
FIG. 17 is a chart showing the effects of cyclolinopeptide A on the expression of the HSP70A gene in *Caenorhabditis elegans*. Bars on the columns represent standard deviations. Letters above the bars designate significant differences determined by data analysis using one-way analysis of variance with pair-wise multiple comparisons were done by the Tukey test.

Induction of Apoptosis in Human Lung Epithelial Cancer Lines with Cyclolinopeptide A, C and E The following example relates to the use of selected purified individual cyclolinopeptides recovered and processed as disclosed herein for modulating the expression of stress genes. Nematode cultures (*Caenorhabditus elegans*) were exposed for two hours to one of DMSO (negative control), 0.1 µM cyclolinopeptide-A, 1.0 µM cyclolinopeptide-A, 10.0 µM cyclolinopeptide-A, and 100.0 µM cyclolinopeptide-A, and then cultured to assess the effects of cyclolinopeptide-A on the expression of the heat shock gene HSP70A by *C. elegans*. The control treatment was unamended culture medium. The results are shown in FIG. 17 wherein it is evident that addition of 0.1 µM or d 10.0 µM of cyclolinopeptide-A to the culture media resulted in a 30% increase in the production of the Hsp70A protein, while addition of 1.0 µM resulted in a 3.5-fold increase in the production of this heat shock protein.

Example 19

Induction of Apoptosis in Human Lung Epithelial Cancer Lines with Cyclolinopeptide A, C and E The following example disclosed herein relates to a method for showing the association of cyclolinopeptides with the induction of apoptosis in cancer cell lines.

Cell culture. Human bronchial epithelial adenocarcinoma cell line (Calu-3) was obtained from ATCC (Manassas, Va., USA) and cultured in 50 cm$^2$ plastic culture flasks in modified eagle's medium (MEM) supplemented with 10% fetal bovine serum, glutamine (4 mM; Sigma-Aldrich, Canada) and penicillin (100 U mL-1)-streptomycin (100 µg mL-1) solution (Sigma-Aldrich, Canada). Cells were cultured at an initial density of 106 cells/mL, and fresh media was added on day 3. Cells were grown in an incubator at 37° C., 5% $CO_2$, and 100% humidity.

Chemical treatments. Calu-3 cells were treated with different concentrations (0-100 µM) of cyclolinopeptide A ("CLA"), cyclolinopeptide C ("CLC") or cyclolinopeptide E ("CLE"). Camptothecin (Sigma-Aldrich, Canada; 4 µM) and dimethylsulfoxide (DMSO) were used as positive and negative controls, respectively. Camptothecin is useful as a positive control in studies testing the effect of certain compounds on apoptosis in cancer cell lines. Camptothecin is a cytotoxic quinoline alkaloid that inhibits the DNA enzyme topoisomerase I (topo I) and has shown remarkable anti-cancer activity. Two analogs of camptothecin have been approved and are used in cancer chemotherapy. DMSO is a common negative control and is used as a solvent for dissolving peptides as peptides do not dissolve in water.

Figure 14:
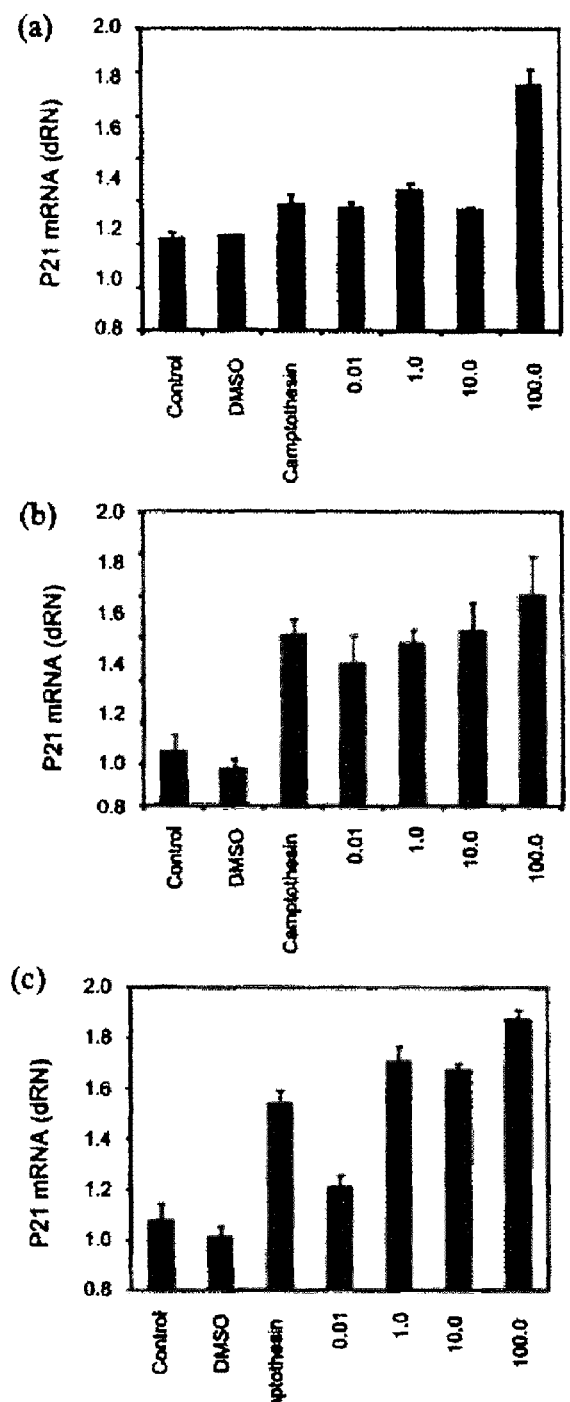
FIG. 14 comprises charts showing the effects of: (a) cyclolinopeptide A on the expression of the P21 gene, (b) cyclolinopeptide C on the expression of the P21 gene, and (c) cyclolinopeptide E on the expression of the P21 gene. DMSO was used as a negative control and camptothecin as a positive control. Bars on the columns represent standard deviations.
Figure 15:
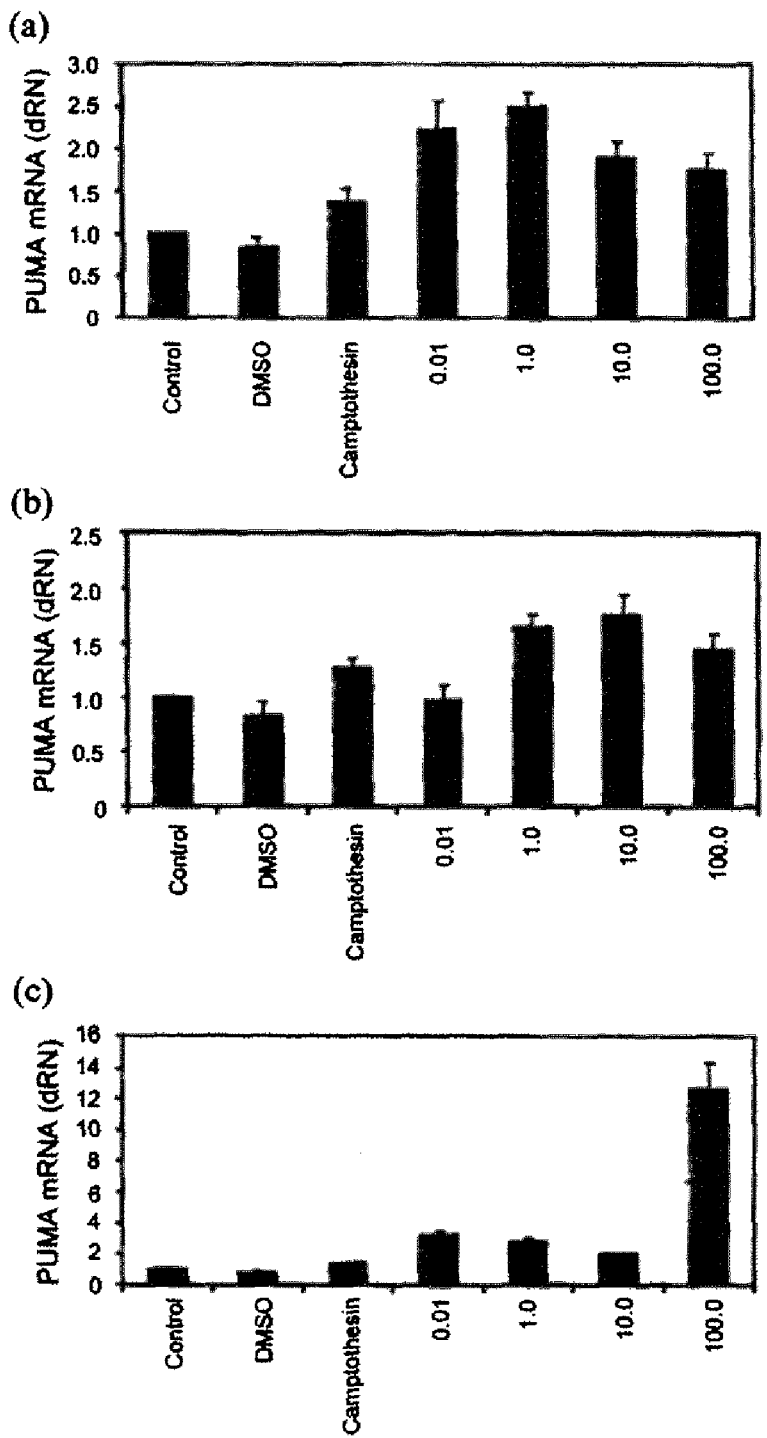
FIG. 15 comprises charts showing the effects of: (a) cyclolinopeptide A on the expression of the p53 upregulated modulator of the apoptosis (PUMA) gene, (b) cyclolinopeptide C on the expression of the PUMA gene, and (c) cyclolinopeptide E on the expression of the PUMA gene. DMSO was used as a negative control and camptothecin as a positive control. Bars on the columns represent standard deviations.
Figure 16:
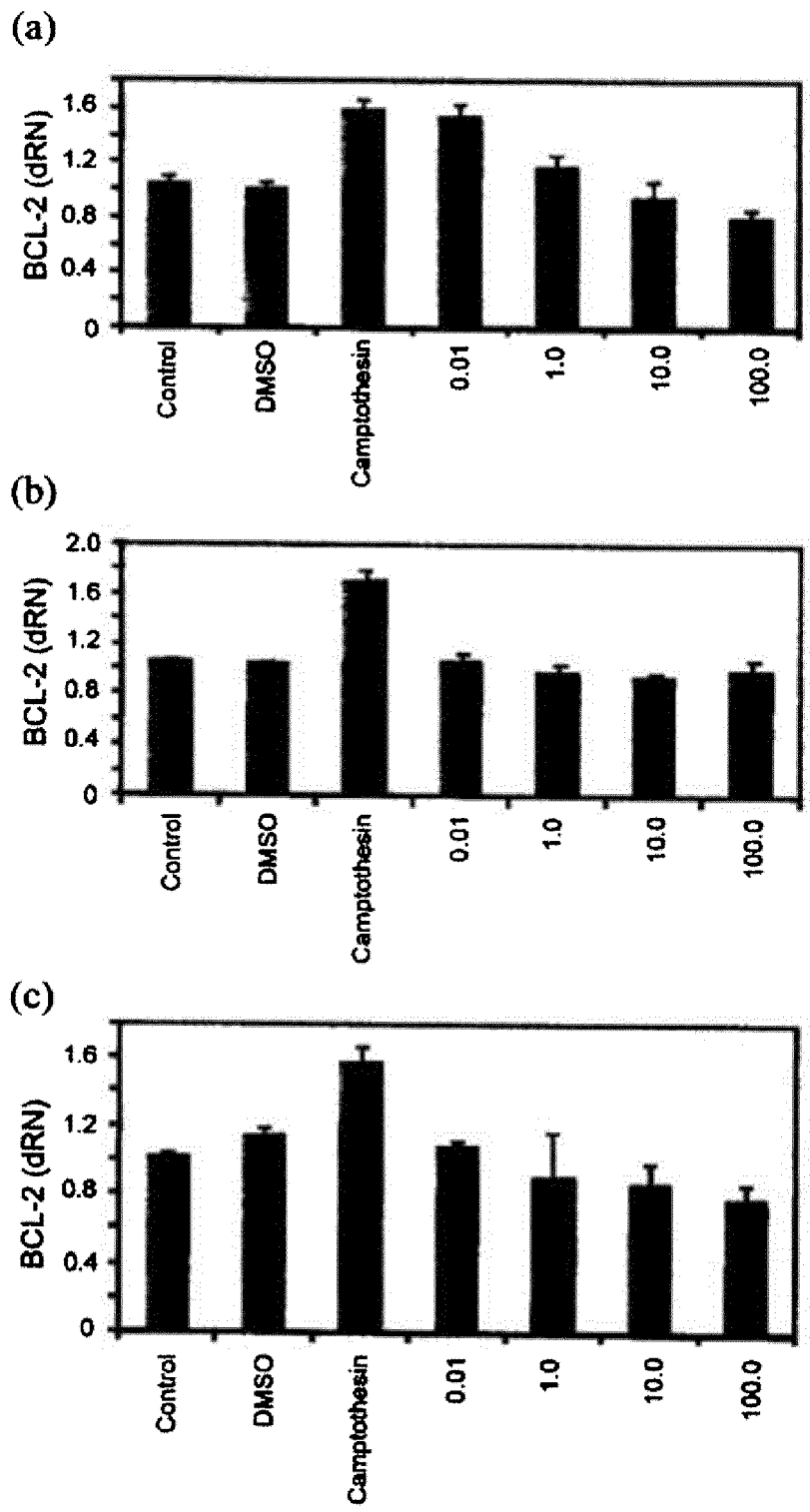
FIG. 16 comprises charts showing the effects of: (a) cyclolinopeptide A on the expression of the BCL-2 alpha gene, (b) cyclolinopeptide C on the expression of the BCL-2 alpha gene, and (c) cyclolinopeptide E on the expression of the BCL-2 alpha gene. DMSO was used as a negative control and camptothecin as a positive control. Bars on the columns represent standard deviations.

Quantitative Real Time Reverse-Transcriptase Polymerase Chain Reaction (qRTPCR). RNA was extracted by using RNeasy® Mini kit (RNeasy is a registered trademark of Qiagen GmbH Corp., Hilden, Fed. Rep. Germany) according to manufacturer's instructions. Integrity of RNA was confirmed by agarose gel electrophoresis and RNA was quantified by NanoDrop® spectrophotometer (NanoDrop is a registered trademark of NanoDrop Techologies LLC, Wilmington, Del., USA). Following DNase treatment, the mRNA was reverse transcribed at 42° C. for 30 min by using QuantiTect® Reverse Transcription kit (QuantiTect is a registered trademark of Qiagen GmbH Corp., Hilden, Fed. Rep. Germany) as per manufacturer's instructions. This cDNA was used for qRTPCR for the expression of tumor necrosis factor alpha (P21; GenBank Accession No. S67388) (FIG. 14), PUMA (GenBank Accession No. AF354655) (FIG. 15), and BCL-2 alpha (Accession No. NM_000633) (FIG. 16) genes using QuantiFast® SYBR® Green PCR kit (SYBR is a registered trademark of Molecular Probes Inc., Eugene, Oreg., USA) as per manufacturer's instructions. The glyceraldehyde-3-phosphate dehydrogenase gene (GAPDH; GenBank Accession No. NM_002046) was used as the reference housekeeping gene. The reactions were performed using the primer pairs; 5'-ATG TCA GAA CCG GCT GGG-3' (SEQ ID NO: 1) and 5'-TCC CAG GCG MG TCA CCC-3' (SEQ ID NO: 2) for P21, 5'-ATG AAA TTT GGC ATG GGG TCT-3' (SEQ ID NO: 3) and 5'-GCC TGG TGG ACC GCC C-3' (SEQ ID NO: 4) for PUMA, 5'-ATG GGG AAG GTG AAG-3'(SEQ ID NO: 5) and 5'-GAC AAG CTT CCC GTT CTC-3' (SEQ ID NO: 6) for GAPDH and 5'-ATG GCG CAC GCT GGG AGA AC-3' (SEQ ID NO: 7) and 5'-GCG ACC GGG TCC CGG GAT GC-3' (SEQ ID NO: 8) for BCL-2. Realtime PCR analysis was performed using the MX3005P® LightCycler® (MX3005P is a registered trademark of Stratagene California Corp., La Jolla, Calif., USA; LightCycler is a registered trademark of Roche Diagnostics GmbH, Mannheim, Fed. Rep. Germany) programmed for denaturation of cDNA at 95° C. for 5 minutes, followed by amplification of the target DNA through 45 cycles of denaturation at 95° C. for 30 seconds, annealing at 55° C. for 30 seconds and elongation at 60° C. for 45 seconds. Relative expression levels were calculated after correction for expression of GAPDH using MxPro software.

Example 20

Microarray Analysis of the Individual Cyclolinopeptides

Current microarray design platforms facilitate the design of gene expression arrays for analysis of a compound of interest and its impact on a large number of known genes. Cyclolinopeptide A, cyclolinopeptide C and cyclolinopeptide E were therefore used in microarray analysis to determine their effect on under- and over-expression of genes involved in the regulation of apoptosis in human lung adenocarcinoma cells (Table 2).

TABLE 2

List of genes up- or down-regulated in human lung adenocarcinoma cells (Calu-3) exposed to CLP-A, -C and -E. '+' and '−' indicates genes over- and under-expressed, respectively.

| Genes | CLP-A | CLP-C | CLP-E |
|---|---|---|---|
| CDEB | + | + | + |
| BAK | + | n/a | n/a |
| Fas | + | + | + |
| FASLG | + | n/a | n/a |
| TNF | + | + | + |
| TP53BP2 | + | + | + |
| TP53 | + | + | n/a |
| CASP10 | n/a | + | n/a |
| CIDEA | n/a | + | + |
| HRK | n/a | + | + |
| BCL-2 | + | − | − |

The genes selected for microarray examination were either pro- or anti-apoptotic genes, including the following: (i) BAK (Bcl-2 homologous antagonist/killer), a pro-apoptotic gene of the Bcl-2 family; (ii) Fas ligand (FASLG) and Fas receptor, wherein the binding of Fas ligand with its receptor induces apoptosis; (iii) TNF (tumor necrosis factor alpha or P21—as described above); (iv) TP53BP2 gene, which encodes a member of the ASPP (apoptosis-stimulating protein of p53) family of p53-interacting proteins; (v) TP53 gene, which encodes p53, a tumor suppressor protein involved in preventing cancer and able to initiate apoptosis if DNA damage proves to be irreparable; (vi) CASP10, which encodes a cysteine-aspartic acid protease that plays a central role in the execution-phase of cell apoptosis; (vii) CIDEA, which encodes the homolog of the mouse protein CIDEA that has been shown to activate apoptosis; (viii) HRK, a pro-apoptotic gene, which encodes a protein that regulates apoptosis through interaction with death-repressor proteins; and (ix) BCL-2, which can either encode pro- or anti-apoptotic proteins.

Example 21

Recrystallization of Cyclinopeptide A

Figure 18:
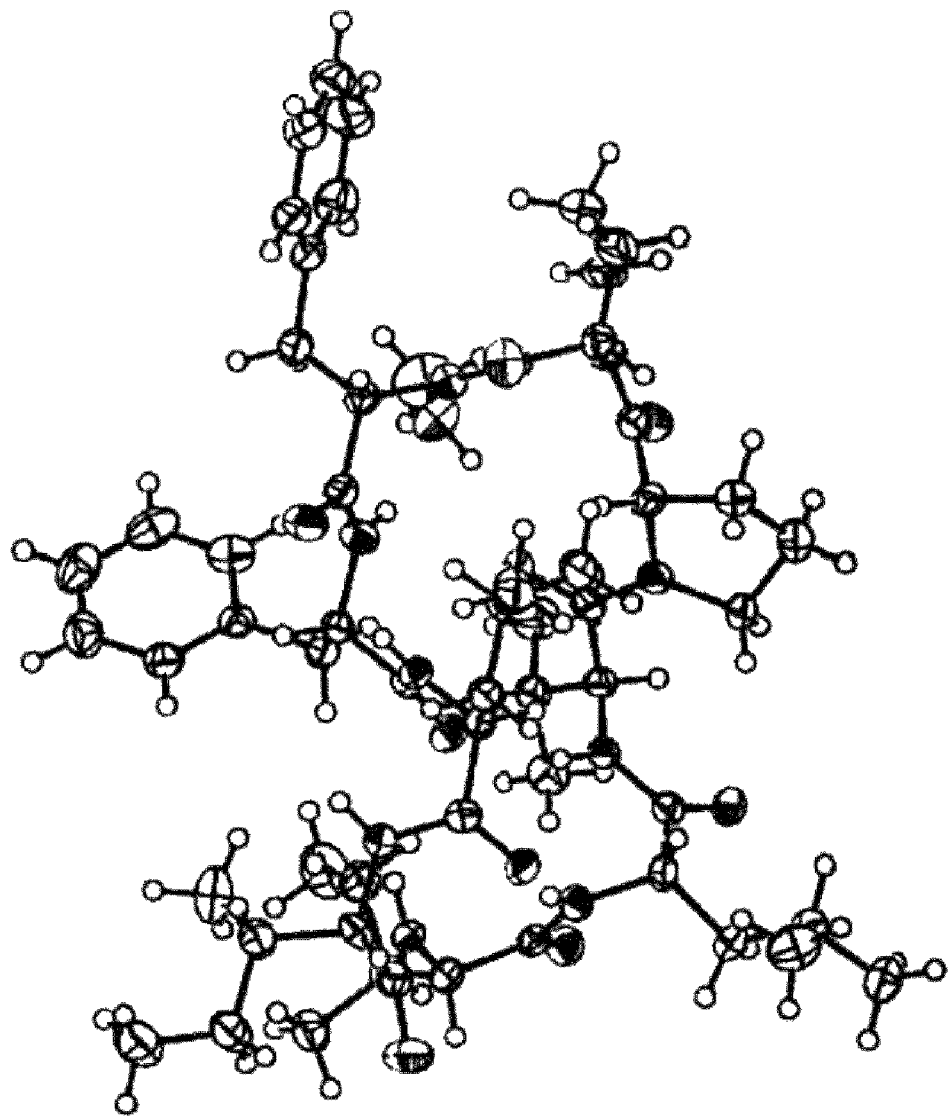
FIG. 18 is an illustration showing the three-dimensional structure of cyclolinopeptide-A, produced by X-ray analysis of cyclolinopeptide-A crystals produced by exemplary methods of the present invention.

A 50-mg sample of cyclinopeptide-A (50 mg) separated and recovered from flaxseed oil according to the method described in Example 8, was dissolved in 5 mL of methanol at about 22° C. A 0.2 mL aliquot of water was slowly added into the cyclolinopeptide-methanol solution and the resulting mixture was then slowly evaporated. Cyclinopeptide-A crystals began forming after about 48 h. A sample of cyclinopeptide-A crystals thus produced was examined with an X-ray analysis system. FIG. 18 shows the three-dimensional structure cyclinopeptide-A, produced by the Z-ray analysis.

While this invention has been described with respect to the exemplary embodiments, it is to be understood that various alterations and modifications to the methods can be made to the exemplary embodiments disclosed herein, which are limited only by the scope of the appended claims.

The invention claimed is:

1. A method for separation and recovery of cyclic peptides from flax, said method comprising the steps of:
    separating an endogenous oil from flax using a physical method selected from the group consisting of pressing, grinding, extruding, blending, tempering, exposure to ultrasound, exposure to microwaves, and exposure to infrared radiation;
    commingling the separated oil directly with a suitable adsorbent whereby the cyclic peptides attach to the adsorbent;
    washing the adsorbent at least once with a suitable solvent selected for solubilising at least one plurality of cyclic peptides attached to the adsorbent; and
    recovering the at least one plurality of cyclic peptides from the solvent.

2. The method according to claim 1, wherein an oil is commingled with flax prior to separating the endogenous oil.

3. The method according to claim 1, wherein the plant part of flax is selected from the group consisting of seeds, nuts, roots, fruits, fruit pulp, stems, latex, and leaves.

4. The method according to claim 3, wherein the plant part of flax is flaxseed.

5. The method according to claim 1, wherein the method further comprises limiting exposure of the oil to oxygen during the separation of the oil, and during separation of cyclic peptides from the separated oil.

6. The method according to claim 1, wherein the at least one plurality of cyclic peptides is solubilised using a solvent comprising one of a hydrocarbon, a ketone, a lower aliphatic alcohol, an ester, a halogenated solvent, an ether, an aromatic selected, and combinations thereof.

7. The method according to claim 6, wherein the hydrocarbon is selected from the group consisting of propane, butane, hexane and isomers thereof.

8. The method according to claim 3, wherein the ketone is selected from the group consisting of acetone, 2-butanone and methyl ethyl ketone.

9. The method according to claim 6, wherein the lower aliphatic alcohol is selected from the group consisting of methanol, ethanol, n-propanol, isopropanol, n-butanol, sec-butanol, t-butanol, amyl-alcohol, isoamyl alcohol and active amyl alcohol.

10. The method according to claim 6, wherein the ester is selected from the group consisting of ethyl acetate and glyceroltriacetate.

11. The method according to claim 6, wherein the halogenated solvent is selected from the group consisting of chloroform, methylene chloride and carbon tetrachloride.

12. The method according to claim 6, wherein the ether is selected from the group consisting of dioxan, tetrahydrofuran, dimethyl ether and diethyl ether.

13. The method according to claim 6, wherein the aromatic is selected from the group consisting of benzene, xylene and toluene.

14. The method according to claim 1, wherein a series of solvents is sequentially flowed through the adsorbent whereby each solvent is selected for solubilising at least one plurality of cyclic peptides attached to the absorbent adsorbent.

15. The method according to claim 1, wherein the at least one plurality of cyclic peptides is purified and optionally refined to recover individual cyclic peptides.

16. The method according to claim 15, wherein the individual cyclic peptides are purified using a physical method selected from a group consisting of silica-gel column chromatography, high performance liquid chromatography and reversed-phase chromatography.

17. The method according to claim 1, wherein the suitable adsorbent is silica.

18. The method according to claim 17, wherein the silica is washed with a series of increasing polarity solvents, wherein each solvent is selected for solubilisation and elution of specific cyclic peptides.

19. The method according to claim 18, wherein each elution is flowed through chromatography equipment to further separate and purify individual cyclic peptides.

20. The method according to claim 1, wherein recovery of cyclic peptides from flax is increased compared with methods comprising extraction of the oil with one or more solvents prior to commingling with a suitable adsorbent.

* * * * *

UNITED STATES PATENT AND TRADEMARK OFFICE
CERTIFICATE OF CORRECTION

| | |
|---|---|
| PATENT NO. | : 8,383,172 B2 |
| APPLICATION NO. | : 12/747160 |
| DATED | : February 26, 2013 |
| INVENTOR(S) | : Martin J. Reaney et al. |

It is certified that error appears in the above-identified patent and that said Letters Patent is hereby corrected as shown below:

In the Claims

Column 20, line 60, "absorbent adsorbent", should read --adsorbent--.

Signed and Sealed this
Fifth Day of November, 2013

Teresa Stanek Rea
*Deputy Director of the United States Patent and Trademark Office*